United States Patent
Eriksson

(10) Patent No.: US 8,383,112 B2
(45) Date of Patent: Feb. 26, 2013

(54) TARGETING VEGF-B REGULATION OF FATTY ACID TRANSPORTERS TO MODULATE HUMAN DISEASES

(75) Inventor: Ulf Eriksson, Stockholm (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 13/343,493

(22) Filed: Jan. 4, 2012

(65) Prior Publication Data

US 2012/0114642 A1 May 10, 2012

Related U.S. Application Data

(63) Continuation of application No. 12/299,672, filed as application No. PCT/US2007/011788 on May 7, 2007, now Pat. No. 8,114,399.

(60) Provisional application No. 60/801,549, filed on May 17, 2006.

(51) Int. Cl.
*A61K 39/395* (2006.01)
*C12P 21/08* (2006.01)
*C07K 16/22* (2006.01)

(52) U.S. Cl. ............. 424/133.1; 424/141.11; 424/145.1; 530/387.3; 530/388.1; 530/388.23

(58) Field of Classification Search .................. None
See application file for complete search history.

(56) References Cited

U.S. PATENT DOCUMENTS

| | | | |
|---|---|---|---|
| 5,194,596 A | 3/1993 | Tischer et al. | |
| 6,331,301 B1 | 12/2001 | Eriksson et al. | |
| 2005/0282233 A1* | 12/2005 | Eriksson et al. | 435/7.2 |
| 2006/0088882 A1 | 4/2006 | Jain et al. | |
| 2007/0050857 A1 | 3/2007 | Hayward et al. | |
| 2009/0324611 A1 | 12/2009 | Eriksson | |

FOREIGN PATENT DOCUMENTS

| WO | WO-9626736 A1 | 9/1996 |
|---|---|---|
| WO | 0164233 * | 9/2001 |

OTHER PUBLICATIONS

Li et al, Trends in Molecular Medicine 18(2): 119-127, Feb. 2012.*
Yu et al, Investigative Ophthalmology & Visual Science 49(2): 522-527, Feb. 2008.*
King et al, Br J Pharmacol, "The use of mouse models in diabetes research", abstract only, Epub Feb. 21, 2012.*
L.A. Cogburn et al., Journal of Nutrition 119:1213, Apr. 1989.*
Scotney et al. "Human vascular endothelial growth factor B: characterization of recombinant isoforms and generation of neutralizing monoclonal antibodies." Clinical and Experimental Pharmacology and Physiology 29(11): 1024-1029. (Nov. 2002).
Mould et al. "Prophylactic but not therapeutic activity of a monoclonal antibody that neutralizes the binding of VEGF-B to VEGFR-1 in a murine collagen-induced arthritis model." Rheumatology 47(3): 263-266. (Mar. 2008).
Fisher et al: "Fatty acid transport proteins and insulin resistance." Current Opinion in Lipidology 16(2): 173-178. (Apr. 2005).
Leonard et al: "Crystal Structure of Vascular Endothelial Growth Factor-B in Complex with a Neutralising Antibody Fab Fragment." Journal of Molecular Biology 384(5): 1203-1217. (Dec. 2008).
Hagberg, Carolina. "Vascular Metabolomics—Role of VEGF-B in fatty acid uptake and metabolic disease." Karolinska Institutet, Stockholm, Sweden. (Apr. 2011).
Yu et al, "Interaction between Bevacizumab and Murine VEGF-A: A Reassessment" Investigative Ophthalmology & Visual Science 49(2): 522-527. (2008).
Zhu et al, "Inhibition of tumor growth and metastasis by targeting tumor-associated angiogenesis with antagonists to the receptors of vascular endothelial growth factor." Investigational New Drugs 17: 195-212. (1999).
Cogburn et al, "Growth, Metabolic and Endocrine Responses of Broiler Cockerels Given a Daily Subcutaneous Injection of Natural or Biosynthetic Chicken Growth Hormone" Journal of Nutrition 119:1213-1222. (1989).
Hagberg et al, "Vascular endothelial growth factor B controls endothelial fatty acid uptake." Nature 464: 917-924. (2010).
Benjamin et al, "A plasticity window for blood vessel remodelling is defined by pericyte coverage of the preformed endothelial network and is regulated by PDGF-B and VEGF" Development 125: 1591-1598. (1998).
Witkowski et al, "Conversion of a beta-ketoacyl synthase to a malonyl decarboxylase by replacement of the active-site cysteine with glutamine." Biochemistry 38(36): 11643-11650. (1999).
Samuel et al, "Mechanism of Hepatic Insulin Resistance in Non-alcoholic Fatty Liver Disease" J. Biol. Chem., vol. 279, Issue 31, 32345-32353. (2004).
Kamba et al., "VEGF-dependent plasticity of fenestrated capillaries in the normal adult microvasculature," Am J Physiol Heart Circ Physiol 290: H560-H576. (2006).

* cited by examiner

*Primary Examiner* — Phuong Huynh
(74) *Attorney, Agent, or Firm* — Fox Rothschild LLP

(57) ABSTRACT

The present invention provides materials and methods for modulating FATP expression and/or activity in vivo. The materials and methods have numerous diagnostic, prophylactic, and therapeutic applications for various diseases and conditions that are influenced by FATPs, or characterized by excessive or inadequate FATP expression or activity.

30 Claims, No Drawings

TARGETING VEGF-B REGULATION OF FATTY ACID TRANSPORTERS TO MODULATE HUMAN DISEASES

CROSS REFERENCE TO RELATED APPLICATION

This application is a continuation of U.S. patent application Ser. No. 12/299,672, now U.S. Pat. No. 8,114,399, having a 371(c) filing date of Apr. 17, 2009, which is the U.S. National Phase of International Patent Application Serial No. PCT/US2007/011788, filed May 7, 2007, which, in turn, claims priority to U.S. Provisional Patent Application Ser. No. 60/801,549, filed May 17, 2006, the disclosures of which are incorporated herein by reference in their entireties.

BACKGROUND OF THE INVENTION

Fatty acid transport proteins (FATP) are membrane-bound proteins that transport free fatty acids (FFA) across the plasma membrane, and are thus responsible for cellular uptake of FFA from the extracellular space. Chiu et al., report that transgenic overexpression of FATP1 in the heart leads to increased lipid uptake, lipotoxicity, and cardiac myopathy (Circ. Res., 96:225-233, 2005). Chiu et al. illustrate the critical need for a controlled uptake of FFA to tissues. Accumulated FFA are not properly oxidized can be toxic to cells.

Lipid accumulation in tissues, particularly of skeletal muscle, has also been suggested to induce insulin resistance syndrome (also know as the diabetic metabolic syndrome). FATP4 has been shown by linkage analysis to be a candidate gene in the insulin resistance syndrome characterized by dyslipidemia, hypertension, and the procoagulant state (Gertow et al., Clin. Endocrinol. Metab., 89:392-399, 2004, the disclosure of which is incorporated herein by reference). Similarly, FATP1 has been linked with elevated post-prandial lipaemia and alterations in LDL particle size distribution Gertow et al., Atherscler., 167:265-273, 2003, the disclosure of which is incorporated herein by reference). A review of fatty acid transport proteins and their role in insulin resistance can be found in Fisher et Ed., Curr. Opin. Lipidol., 16:173-178, 2005, the disclosure of which is incorporated herein by reference.

Aberrant lipid accumulation is closely related to deleterious lipotoxic effects, insulin resistance, perturbations of both lipid and carbohydrate metabolism and other features of the metabolic syndrome (Unger et al., Endocrinol., 144:5159-5164, 2004, the disclosure of which is incorporated herein by reference). Thus, a need exists for new materials and methods for modulating FATP expression and/or activity in vivo, for prophylaxis or therapy of various diseases and conditions that are influenced by FATPs.

SUMMARY OF THE INVENTION

The present invention provides materials and methods for modulating FATP expression and/or activity in vivo. The materials and methods have numerous diagnostic, prophylactic, and therapeutic applications for various diseases and conditions that are influenced by FATPs, or characterized by excessive or inadequate FATP expression or activity.

For example, in embodiment, the invention is a method of reducing lipid accumulation in any mammalian subject that has any disease or condition for which lipid reduction is a desirable therapeutic goal (as well as for subjects at risk for developing such disease or condition). In one variation, the method comprises administering to a mammalian subject in need of treatment to reduce lipid accumulation a composition that comprises a VEGF-B inhibitor, in an amount effective to reduce lipid accumulation in a tissue in the subject.

In these and other embodiments of the invention, the method optionally further includes one or more steps of monitoring one or more parameters in the subject, to confirm the safety and/or efficacy of the treatment and/or to optimize dosing. Thus, for example, in a method of the invention for reducing lipid accumulation, the method optionally further comprising monitoring lipid markers in a biological sample comprising a tissue or fluid from the subject. Exemplary tissues include biopsies of any organ (liver, kidney, spine, heart, vessel, intestine, etc) or skin or hair, for example. Exemplary fluids include blood, cerebrospinal fluid, semen, saliva, or other secretions or excretions.

Another aspect of the invention is a method of stimulating glucose metabolism in a mammalian subject, comprising administering to a mammalian subject in need of treatment for a condition characterized by elevated blood glucose a composition that comprises a VEGF-B inhibitor, in an amount effective to increase glucose tolerance and/or reduce insulin resistance in the subject. Glucose metabolism generally may be tracked via glucose measurements in the blood or serum of the subject. In some variations, the method further includes monitoring glucose levels in the blood of the subject. The administration (dose, dosing frequency) is modulated to balance maximum therapeutic benefit with minimization of side-effects.

For methods described herein in which involve a subject in need of treatment or prophylaxis for a particular condition, the method of the invention includes selecting a patient based on appropriate criteria (e.g., medical diagnosis based on accepted tests, family history, examination, and other criteria) for the prophylaxis or therapy. Thus, for example, the methods summarized above may further comprise selecting for treatment a subject with at least one disease or condition selected from the group consisting of: obesity, insulin resistance, diabetes, hepatic steatosis and metabolic syndrome. In some variations, the subject has type II diabetes.

Numerous exemplary VEGF-B inhibitors are described below in greater detail, for use in methods of the invention that require them. Exemplary VEGF-B inhibitors include, but are not limited to:

(a) antibodies that immunoreact (bind) with VEGF-B (also known as VEGF-B antibodies or anti-VEGF-B antibodies); such antibodies include antibodies that bind multiple isoforms of VEGF-B, as well as antibodies that show preferential binding or specificity for one isoform, such as a VEGF-$B_{167}$ antibody or a VEGF-$B_{186}$ antibody;

(b) a VEGFR-1 antibody (preferably one that immunoreacts with the extracellular domain of VEGFR-1);

(c) fragments of (a) or (b) that retain antigen binding activity;

(d) polypeptides that comprise an antigen binding domain of (a), (b) or (c) and that bind said antigen;

(e) antisense oligonucleotides that inhibit VEGF-B transcription or translation;

(e) aptamers that inhibit VEGF-$B_{167}$ and/or VEGF-$B_{186}$;

(f) short interfering RNA (siRNA, RNAi) that inhibits VEGF-B translation; and, (g) small molecule inhibitors of VEGFR-1.

Antibodies and other binding agents (and antigen binding domains thereof) for use as described herein bind selectively to antigen (such as VEGF-B), which means they bind preferentially to antigen with a greater binding affinity than with which they bind other antigens. In some variations, the antibodies or other binding agents are antigen-specific binding agents that are capable of distinguishing antigen from other closely related members of the same family of proteins (e.g., other VEGF/PDGF family members). Typically, the antigen binding agents for use in practicing the invention (or fragments, variants, or derivatives thereof of) will bind with a greater affinity to human antigen (when selected for human treatment/medicaments) as compared to its binding affinity to antigen of other, e.g, non human, species. However, it is to be expected that antibodies that are specific for a human protein (e.g., VEGF-B or VEGFR-1) may also bind, to varying degrees, to species homologs of the same protein.

The term "antigen binding domain" or "antigen binding region" refers to that portion of the selective binding agent (such as an antibody molecule) which contains the specific binding agent amino acid residues that interact with an antigen and confer on the binding agent its specificity and affinity for the antigen. In an antibody, the antigen binding domain is commonly referred to as the "complementarity determining region, or CDR."

In still another embodiment, the invention is a method of improving tissue or organ transplantation in a mammalian subject, comprising: contacting a transplant tissue or organ with a composition, or administering to a transplant recipient the composition, said composition comprising a healing agent selected from the group consisting of Vascular Endothelial Growth Factor B (VEGF-B) polynucleotides and VEGF-B polypeptides, wherein the healing agent is present in said composition in an amount effective to increase nutrient supply to the tissue or organ.

In the context of this method and other methods of the invention involving therapeutic administration, the term "VEGF-B polypeptide" should be understood to mean a soluble form of VEGF-B that retains a characteristic VEGF-B biological activity, such as binding to VEGFR-1 expressed on the surface of cells. Another characteristic VEGF-B activity that is important to the invention is VEGF-B's effects on modulating FATP proteins, described herein in detail. The term VEGF-B polypeptide likewise refers to pro-forms of the polypeptide that may be cleaved in vivo into active forms; and polypeptides that are chemically modified, e.g., to improve serum half-life or stability. The term "VEGF-B polynucleotide" refers to polynucleotides that encode a VEGF-B polypeptide. Such polynucleotides include "naked DNA" constructs, and also various vectors that contain/include the encoding polynucleotide sequence. The polynucleotide preferably includes one or more suitable expression control sequences, such as promoters, to promote expression of the encoded polypeptide in cells of the mammalian subject to be treated.

Some variations of this method include co-therapy with additional agents. For example, in some variations, the method further comprises administering at least one additional agent selected from the group consisting of Vascular Endothelial Growth Factor (VEGF) polynucleotides, VEGF polypeptides, Vascular Endothelial Growth Factor C (VEGF-C) polynucleotides, VEGF-C polypeptides, Vascular Endothelial Growth Factor D (VEGF-D) polynucleotides, and VEGF-D polypeptides, and Platelet Derived Growth Factor A, B, C, or D polypeptides or polynucleotides, wherein the additional agent is administered in an amount effective to reduce edema or increase perfusion into the transplanted tissue or organ, thereby improving the healing thereof. The polypeptides and polynucleotides of this paragraph have similar definitions as ascribed to VEGF-B polypeptides/polynucleotides in the preceding paragraph, adjusted to reflect the known activities of the particular polypeptide. Thus, for example, VEGF-C polypeptides are those that retain the characteristic ability of VEGF-C to bind to its receptor, VEGFR-3, through which VEGF-C has been shown to exhibit lymphangiogenic effects. In all instances, human sequences are preferred.

In still another variation, the method optionally includes administering one or more immunosuppressants to prevent graft-versus-host "rejection" of the transplant.

Still another aspect of the invention is a method of treatment or prophylaxis for a neurodegenerative disorder in a mammalian subject. One exemplary method comprises: administering to a mammalian subject in need of treatment or prophylaxis for a neurodegenerative disorder a composition comprising an agent selected from the group consisting of Vascular Endothelial Growth Factor B (VEGF-B) polynucleotides and VEGF-B polypeptides. The agent preferably is present in said composition (and administered) in an amount effective to inhibit neurodegeneration in the subject. A number of diseases and disorders for treatment are described below in greater detail.

A further aspect of the invention is a method of treatment or prophylaxis for cachexia in a mammalian subject. An exemplary method comprises: administering to a mammalian subject in need of treatment or prophylaxis for cachexia a composition comprising an agent selected from the group consisting of Vascular Endothelial Growth Factor B (VEGF-B) polynucleotides and VEGF-B polypeptides, wherein the agent is present in said composition in an amount effective to stimulate lipid accumulation in tissues in the subject, thereby slowing, halting, or even reversing the cachexia.

In some variations, the mammalian subject for treatment or prophylaxis for cachexia is identified as having a cancer characterized by cells that produce a soluble VEGFR-1 polypeptide. For such subjects, the invention preferably further comprises administering to the subject a second agent that comprises an antibody that binds soluble VEGFR-1. To improve the efficacy of the antibody, in some variations, the antibody that binds soluble VEGFR-1 is conjugated (attached) to a polypeptide selected from the group consisting of VEGF polypeptides, VEGF-C polypeptides, VEGF-D polypeptides, PDGF-A polypeptides, PDGF-B polypeptides, PDGF-C polypeptides, PDGF-D polypeptides, and P1GF polypeptides, wherein said antibody conjugate retains the ability to bind soluble VEGFR-1.

In this context, the term "soluble VEGFR-1" should be understood to be a polypeptide that includes all or a portion of the VEGFR-1 extracellular domain, and that can bind one or more VEGF-B isoforms. The soluble VEGFR-1 is lacking all or a portion of the VEGFR-1 transmembrane and intracellular domains, rendering it soluble in the blood.

In some variations, a ligand (e.g., polypeptides, antibodies, etc.) may be coated with beads and administered in vivo as described in Ueng et al., I. Orthopeedic Research, 22:592-599, 2006 and Kumar, M., J. Pharm. Pharmaceut. Sci., 3:234-258, 2000, the disclosures of which are incorporated herein by reference in their entireties for the treatment or prophylaxis of cachexia.

In yet another, related embodiment, the invention is a method of treatment or prophylaxis for cachexia comprising: administering to a mammalian subject in need of treatment or prophylaxis for cachexia a composition comprising an agent that comprises an antibody that binds to soluble VEGFR-1, in an amount effective to stimulate lipid accumulation in tissues of the subject. As already described, the antibody preferably is conjugated to a polypeptide selected from the group consisting of VEGF polypeptides, VEGF-C polypeptides, VEGF-D polypeptides, PDGF-A polypeptides, PDGF-B polypeptides, PDGF-C polypeptides, PDGF-D polypeptides, and P1GF polypeptides. In some variations, the mammalian subject has a neoplastic disease characterized by production of soluble VEGFR-1 that circulates in blood of the subject. In some variations, co-therapy with a VEGF-B polynucleotide or polypeptide is specifically contemplated.

For aspects of the invention that involve VEGF-B polypeptides or polynucleotides, human polypeptide sequences are preferred, yet analogs that retain VEGF-B biological activity also are contemplated. Thus, in some variation; the agent comprises, for example:

(a) a polypeptide that comprises an amino acid sequence that is at least 90%, or 95%, or 97.5%, or 99% identical to the amino acid sequence of amino acids 22 to 188 of SEQ ID NO: 3, which constitutes a human sequence for VEGF-$B_{167}$;

(b) a polypeptide that comprises an amino acid sequence that is at least 90%, or 95%, or 97.5%, or 99% identical to the amino acid sequence of amino acids 22 to 207 of SEQ ID NO: 4, which constitutes a human sequence for VEGF-$B_{186}$;

(c) a polynucleotide that comprises a nucleotide sequence that encodes (a) or (b).

Exemplary polynucleotides for practicing the invention include expression vectors, such as "gene therapy" vectors, that comprise the polynucleotide that encodes the desired polypeptide. Exemplary expression vectors include adenoviral vectors, adeno-associated viral vectors, and lentivirus vectors. Replication-deficient forms of the vectors are preferred.

Numerous aspects of the invention have been described in the context of methods of treatment. For each such method, a related aspect of the invention is use of the agent (described in the method) for the manufacture of a medicament for treatment or prophylaxis for the specified disease or conditions.

For example, the invention includes use of a VEGF-B inhibitor in the manufacture of a medicament to reduce lipid accumulation in a mammalian subject.

The invention also includes use of a VEGF-B inhibitor in the manufacture of a medicament to stimulate glucose metabolism in a mammalian subject.

In related aspects, the invention includes use of a VEGF-B inhibitor in the manufacture of a medicament for the treatment or prophylaxis of a disease or condition selected from the group consisting of obesity, insulin resistance, diabetes, hepatic steatosis, metabolic syndrome, lipid accumulation in the kidney, lipid accumulation in the heart or skeletal muscle, and lipid accumulation in other organs.

The invention further includes use of a VEGF-B polynucleotide or VEGF-B polypeptide in the manufacture of a medicament for improving tissue or organ transplantation in a mammalian subject.

The invention also is directed to use of a VEGF-B polynucleotide or VEGF-B polypeptide in the manufacture of a medicament for the treatment or prophylaxis of a neurodegenerative disorder in a mammalian subject.

A further aspect of the invention is directed to use of a VEGF-B polynucleotide or VEGF-B polypeptide in the manufacture of a medicament for the treatment or prophylaxis of any of the neurodegenerative disorders described herein.

Still another aspect of the invention is directed to use of a VEGF-B polynucleotide or polypeptide in the manufacture of a medicament for the treatment or prophylaxis of cachexia in a mammalian subject.

The invention further provides a method of inhibiting expression of fatty acid transport proteins (FATPs) in a mammalian subject comprising administering to said subject a composition comprising a VEGF-B inhibitor in an amount effective to inhibit expression of FATPs in said subject. In one embodiment, the FATPs are selected from the group consisting of FATP1, FATP3, FATP4, FATP6, LPL, and combinations thereof. In another embodiment the FATP is selected from the group consisting of FATP4, LPL and combinations thereof.

The invention also provides a method of inhibiting tumor cell growth in a mammalian subject comprising administering to said subject a composition comprising a VEGF-B inhibitor in an amount effective to decrease FATP expression and thereby inhibit tumor cell growth in said subject. In one embodiment, the VEGF-B inhibitor is an inhibitor of VEGF-$B_{186}$, and/or the FATP is FATP1.

For all therapeutic and prophylactic methods described herein, exemplary mammalian subjects include humans and animals of economic importance for farming, food, livestock, transportation, pets, zoos, pre-clinical medical work. Exemplary animals include dogs/canines, cats/felines, primates, pigs/porcines, cows/bovines, horses/equines, rats, mice, dromedaries, and others.

Suitable compositions for administration further include one or more additional components such as pharmaceutically acceptable diluents, adjuvants, carriers, preservatives, flavorings, or other convention additives described herein and/or known in the field.

Additionally, co-therapies are contemplated as part of the invention. Administration of multiple therapeutics may be simultaneous (in admixture or separate), sequential, or separated in time during a treatment period.

Many of the disease or conditions described herein are chronic in nature and the administration is expected to be repeated over a period that may involve days, weeks, months, years, or even the entire duration of a subject's life.

In jurisdictions that forbid the patenting of methods that are practiced on the human body, the following restrictions are intended: (1) the selecting of a human subject shall be construed to be restricted to selecting based on testing of a biological sample that has previously been removed from a human body and/or based on information obtained from a medical history, patient interview, or other activity that is not practiced on the human body; and (2) the administering of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the selecting of subjects and the administering of compositions includes both methods practiced on the human body and also the foregoing activities.

Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value or sub-range within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

The FATP family of proteins comprises six members (FATP1-6) with distinct expression patterns. Two of the most relevant tissues to consider in terms of fatty acid metabolism and insulin resistance are adipose tissue and skeletal muscle. FATP1 expression is high in both tissues, whereas FATP4 is much lower (its principal site of expression being the small intestine), but both have been linked to insulin resistance and associated parameters. FATP1 has been linked to insulin resistance and is expressed in adipose tissue and skeletal muscle (Kim et al, J. Clin. Invest., 113:756-763, 2004, the disclosure of which is incorporated herein by reference). FATP2 is located in peroxisomes of the liver and kidney and is implicated in the activation of both bile acids and fatty acids (Mihalik et al., J. Biol. Chem., 277:24771-24779, 2002, the disclosure of which is incorporated herein by reference). FATP4 has also been linked to insulin-resistance related parameters and is expressed in the intestines, liver and adipose tissue. FATPs 2, 3 and 5 are expressed in the liver and kidney. FATP6 is expressed almost exclusively in the heart (Gimeno et al., J. Biol. Chem., 278:16039-16044, 2003, the disclosure of which is incorporated herein by reference).

The present invention demonstrates that several FATPs and endothelial LPL are down-regulated in VEGF-B deficient animals, and conversely some FATPs and LPL are up-regulated in conditions of VEGF-B over-expression. These data suggest that VEGF-B modulates the expression of FATPs and LPL, and thus both the hydrolysis of circulating triglycerides, as well as the uptake of FFA from the bloodstream to various parenchyma. Direct analysis of lipid accumulation in normal and VEGF-B deficient mouse hearts by Oil Red O staining verify this possibility, as abundant lipid droplets are visualized in tissue sections from normal animals, while tissue sections from VEGF-B deficient animals contain very few, if any lipid droplets. VEGF-B controlled expression of FATP and LPL expression are postulated to have implications in several major diseases like cancer, diabetes, obesity, cardiovascular diseases, and neurological degenerative diseases, like Alzheimer's disease, Parkinson's disease, and amyelotroph lateral sclerosis (ALS).

In cancer, VEGF-B expression (or over-expression) may control the energy status of the tumor cells by providing high energy fuel as FFA, and thus affecting the growth rate, as well as other physiological parameters of tumors (both tumor cells as well as stroma). Furthermore, VEGF-B may have a role in the muscle wasting syndrome, termed cachexia, that affects about 50% of all cancer patients, and is frequently seen in patients with heart or kidney insufficiencies. In cachexia patients, VEGF-B therapy to improve FFA uptake is postulated to have a therapeutic value.

In diabetes, VEGF-B may modulate the uptake of blood lipids to the endothelial cells, and aberrant expression (especially over-expression) may result in dyslipidemia, a condition found in many diabetic patients as part of the metabolic syndrome. In insulin-resistant states such as obesity, fatty acid metabolism and homeostasis are clearly disturbed. Fatty acid clearance and storage capacity in adipose tissue are impaired, and fatty acids may accumulate in the circulation and in nonadipose tissues such as liver skeletal muscle in the form of triacylglycerol, diacylglycerol, ceramides and fatty acyl-CoAs. Such ectopic lipid accumulation is closely related to deleterious lipotoxic effects, insulin resistance, perturbations of both lipid and carbohydrate metabolism and other features of the metabolic syndrome (Unger et al., Endocrinol., 144:5159-5164, 2004, the disclosure of which is incorporated herein by reference).

In cardiovascular disease, VEGF-B is known to stimulate revascularization following a heart infarction (see U.S. Patent Application Publication No.: 2003-0008824, the disclosure of which is incorporated herein by reference), and VEGF-B may have this effect by stimulating the uptake of FFA to the myocardium and indirectly stimulate revascularization by providing a better energy state in the myocardium.

In neurodegenerative diseases like Alzheimer's disease and Parkinson's disease, increasing evidence suggests that part of the pathophysiology of these diseases is a cerebrovascular defect that may manifest in decreased nutritional supply to the neurons, and subsequent neuronal death. Given that VEGF-B is abundantly expressed in brain and may be responsible for at least one aspect of nutrient uptake to cells, i.e., FFA, it is postulated that loss, or down-regulation of VEGF-B may impair FFA uptake to the neurons, and thus causes nutritional insufficiency of the neurons leading to neuronal death. Other neuronal diseases, like ALS, may also be caused by a cerebrovascular defect (Storkebaum et al., Nat. Neurosci., 8:85-92, 2005; Storkebaum et al., Bioessays, 26:943-943, 2004; Storkebaum et al., J. Clin. Invest., 113:14-18, 2004, the disclosure of which are incorporated herein by reference).

VEGF-B Therapeutic Compounds

Vascular endothelial growth factor B (VEGF-B) is abundantly expressed in organs with a high metabolic turnover, like heart, skeletal muscle, brown fat, cerebral cortex and in gastric secreting parietal cells. It is well documented that all of these organs and cells use free fatty acids (FFA) as their main source for energy production under normal physiological conditions. The ultimate source of FFA for most cells is the plasma where serum albumin is the main transport protein. Plasma-derived FFA has to transverse the blood vessel wall to be used by the energy-requiring parenchymal cells of the heart, muscles, brown fat, brain, etc. (Van der Vusse et al., Adv. Exp. Med. Biol., 441:181-191, 1998).

VEGF-B binds to VEGF receptor 1 (VEGFR-1) which is mainly expressed by endothelial cells of the blood vessel wall. VEGF-B deficient animals are largely normal, suggesting that VEGF-B has no major role in the development of the vascular system during embryogenesis, nor has it an essential role in maintenance of the vascular system in adult animals. In certain stress situations (e.g., following an experimentally induced heart infarction), however, VEGF-B deficient animals do not recover and revascularize the infarcted zone of the heart as well as normal mice (U.S. Patent Application Publication No. 2005/0214280, the disclosure of which is incorporated herein by reference.)

The term "VEGF-B" as used in the present invention encompasses those polypeptides identified as VEGF-B in U.S. Pat. No. 6,331,301, which is incorporated herein in its entirety, as well as published U.S. Application No. 2003/0008824. A human VEGF-B cDNA and deduced amino acid sequence are set forth in SEQ ID NOs: 1 and 2, respectively.

VEGF-B comprises, but is not limited to, both the human VEGF-B$_{167}$ (SEQ ID NO: 3) and mouse VEGF-B$_{167}$ (SEQ ID NO: 7) and/or human VEGF-B$_{186}$ (SEQ ID NO: 4) and mouse VEGF-B$_{186}$ (SEQ ID NO: 8) isoforms or a fragment or analog thereof having the ability to bind VEGFR-1. In one embodiment, active analogs exhibit at least 85% sequence identity, preferably at least 90% sequence identity, particularly preferably at least 95% sequence identity, and especially preferably at least 98% sequence identity to the natural VEGF-B polypeptides, as determined by BLAST analysis. The active substance typically will include the amino acid sequence Pro-Xaa-Cys-Val-Xaa-Xaa-Xaa-Arg-Cys-Xaa-Gly-Cys-Cys (where Xaa may be any amino acid) (SEQ ID NO: 9) that is characteristic of VEGF-B. The examples describe in vitro and in vivo assays for confirming that any selected VEGF-B analog has FATP modulating activity. Neuropilin-1 is also contemplated as having FATP modulatin activity as it is a co-receptor for VEGF-B binding to VEGFR-1.

Use of polypeptides comprising VEGF-B sequences modified with conservative substitutions, insertions, and/or deletions, but which still retain the biological activity of VEGF-B is within the scope of the invention. Standard methods can readily be used to generate such polypeptides including site-directed mutagenesis of VEGF-B polynucleotides, or specific enzymatic cleavage and ligation. Similarly, use of peptidomimetic compounds or compounds in which one or more amino acid residues are replaced by a non-naturally-occurring amino acid or an amino acid analog that retains the required aspects of the biological activity of VEGF-B is contemplated.

In addition, variant forms of VEGF-B polypeptides that may result from alternative splicing and naturally-occurring allelic variation of the nucleic acid sequence encoding VEGF-B are useful in the invention. Allelic variants are well known in the art, and represent alternative forms or a nucleic acid sequence that comprise substitution, deletion or addition of one or more nucleotides, but which do not result in any substantial functional alteration of the encoded polypeptide.

Variant forms of VEGF-B can be prepared by targeting non-essential regions of a VEGF-B polypeptide for modification. These non-essential regions are expected to fall outside the strongly-conserved regions of the VEGF/PDGF family of growth factors. In particular, the growth factors of the PDGF/VEGF family, including VEGF-B and the PDGFs, are dimeric, and at least VEGF-A, VEGF-B, VEGF-C, VEGF-D, P1GF, PDGF-A and PDGF-B show complete conservation of eight cysteine residues in the N-terminal domains, i.e. the PDGF/VEGF-like domains. (Olofsson, et al., *Proc. Nat'l. Acad. Sci. USA*, 93:2576-2581 (1996); Joukov, et al., *EMBO J.*, 15:290-298 (1996)). These cysteines are thought to be involved in intra- and inter-molecular disulfide bonding. In addition there are further strongly, but not completely, conserved cysteine residues in the C-terminal domains. Loops 1, 2 and 3 of each subunit, which are formed by intra-molecular disulfide bonding, are involved in binding to the receptors for the PDGF/VEGF family of growth factors. (Andersson, et al., *Growth Factors*, 12:159-64 (1995)).

These conserved cysteine residues are preferably preserved in any proposed variant form, although there may be exceptions, because receptor-binding VEGF-B analogs are known in which one or more of the cysteines is not conserved. Similarly, the active sites present in loops 1, 2 and 3 also should be preserved. Other regions of the molecule can be expected to be of lesser importance for biological function, and therefore offer suitable targets for modification. Modified polypeptides can readily be tested for their ability to show the biological activity of VEGF-B by routine activity assay such as a VEGFR-1 binding assay or an FATP modulating activity assays based on the examples set forth below. Alignment of VEGF-B sequences from multiple species, to identify conserved and variable residues, provides an indication of residues that are more susceptible to alteration without destroying VEGFR-1 binding activity.

Preferably, where amino acid substitution is used, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar or charged residue for another residue with similarly polarity or charge, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted parent amino acid.

Alternatively, conservative amino acids can be grouped as described in Lehninger, (*Biochemistry*, Second Edition; Worth Publishers, Inc. NY: N.Y., pp. 71-77 (1975)) as set out in the following.

Non-Polar (Hydrophobic)
A. Aliphatic: A, L, I, V, P,
B. Aromatic: F, W,
C. Sulfur-containing: M,
D. Borderline: G.
Uncharged-Polar
A. Hydroxyl: S, T, Y,
B. Amides: N, Q,
C. Sulfhydryl: C,
D. Borderline: G.
Positively Charged (Basic): K, R, H.
Negatively Charged (Acidic): D, E.

VEGF-B protein can be modified, for instance, by glycosylation, amidation, carboxylation, or phosphorylation, or by the creation of acid addition salts, amides, esters, in particular C-terminal esters, and N-acyl derivatives. The proteins also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

VEGF-B proteins can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin).

Examples of VEGF-B analogs are described in WO 98/28621 and in Olofsson, et al., *Proc. Nat'l. Acad. Sci. USA*, 95:11709-11714 (1998), both incorporated herein by reference.

VEGF-B polypeptides are preferably produced by expression of DNA sequences that encode them such as DNAs that correspond to, or that hybridize under stringent conditions with the complements of SEQ ID NOS: 1 and 2. Suitable hybridization conditions include, for example, 50% formamide, 5×SSPE buffer, 5×Denhardts solution, 0.5% SDS and 100 µg/ml of salmon sperm DNA at 42° C. overnight, followed by washing 2×30 minutes in 2×SSC at 55° C. Such hybridization conditions are applicable to any polynucleotide encoding one or more of the growth factors of the present invention.

The invention is also directed to an isolated and/or purified DNA that corresponds to, or that hybridizes under stringent conditions with, any one of the foregoing DNA sequences.

The VEGF-B for use according to the present invention can be used in the form of a protein dimer comprising VEGF-B protein, particularly a disulfide-linked dimer. VEGF-B dimers may comprise VEGF-B polypeptides of identical sequence, of different VEGF-B isoforms, or other heterogeneous VEGF-B molecules. The protein dimers for use according to the present invention include both homodimers of VEGF-B and heterodimers of VEGF-B and VEGF polypeptides, as well as other VEGF family growth factors including, but not limited to placental growth factor (P1GF), which are capable of binding to VEGFR-1 (flt-1). The VEGF-B of the present invention also includes VEGF-B polypeptides that have been engineered to contain an N-glycosylation site such as those described in Jeltsch, et al., WO 02/07514, which is incorporated herein in its entirety.

The term "vector" refers to a nucleic acid molecule amplification, replication, and/or expression vehicle in the form of a plasmid or viral DNA system where the plasmid or viral DNA may be functional with bacterial, yeast, invertebrate, and/or mammalian host cells. The vector may remain independent of host cell genomic DNA or may integrate in whole or in part with the genomic DNA. The vector will contain all necessary elements so as to be functional in any host cell it is compatible with. Such elements are set forth below.

A. Preparation of DNA Encoding VEGF-B Polypeptides

A nucleic acid molecule encoding a VEGF-B polypeptide can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook, et al., "Molecular Cloning: A Laboratory Manual," Cold Spring Harbor Laboratory Press, Cold Spring Harbor, N.Y. (1989), by Ausubel, at al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987). In one embodiment, nucleic acid sequences encoding VEGF-B are mammalian sequences. Specifically, nucleic acid sequences encoding VEGF-B are human and other primates.

Chemical synthesis of a VEGF-B nucleic acid molecule can be accomplished using methods well known in the art, such as those set forth by Engels, et al., Angew. Chem. Intl. Ed., 28:716-734 (1989). These methods include, inter alia, the phosphotriester, phosphoramidite and H-phosphonate methods of nucleic acid synthesis. Typically, the nucleic acid molecule encoding the full length VEGF-B polypeptide will be several hundred base pairs (bp) or nucleotides in length. Nucleic acids larger than about 100 nucleotides in length can be synthesized as several fragments, each fragment being up to about 100 nucleotides in length. The fragments can then be ligated together, as described below, to form a full length nucleic acid encoding the VEGF-B polypeptide. One method is polymer-supported synthesis using standard phosphoramidite chemistry.

Alternatively, the nucleic acid encoding a VEGF-B polypeptide may be obtained by screening an appropriate cDNA library prepared from one or more tissue source(s) that express the polypeptide, or a genomic library from any subspecies. The source of the genomic library may be any tissue or tissues from any mammalian or other species believed to harbor a gene encoding VEGF-B or a VEGF-B homologue.

The library can be screened for the presence of the VEGF-B cDNA/gene using one or more nucleic acid probes (oligonucleotides, cDNA or genomic DNA fragments that possess an acceptable level of homology to the VEGF-B or VEGF-B homologue cDNA or gene to be cloned) that will hybridize selectively with VEGF-B or VEGF-B homologue cDNA(s) or gene(s) that is(are) present in the library. The probes preferably are complementary to or encode a small region of the VEGF-B DNA sequence from the same or a similar species as the species from which the library was prepared. Alternatively, the probes may be degenerate, as discussed below.

Where DNA fragments (such as cDNAs) are used as probes, typical hybridization conditions are those for example as set forth in Ausubel, et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1 percent SDS at 55-65° C. Another such stringent buffer is 1 mM $Na_2$ EDTA, 40 mM $NaHPO_4$, pH 7.2, and 1% SDS at about 40-50° C. One other stringent wash is 0.2×SSC and 0.1% SDS at about 50-65° C. Such hybridization conditions are applicable to any polynucleotide encoding one or more of the growth factors of the present invention.

Another suitable method for obtaining a nucleic acid encoding a VEGF-B polypeptide is the polymerase chain reaction (PCR). In this method, poly(A)+RNA or total RNA is extracted from a tissue that expresses VEGF-B. cDNA is then prepared from the RNA using the enzyme reverse transcriptase. Two primers typically complementary to two separate regions of the VEGF-B cDNA (oligonucleotides) are then added to the cDNA along with a polymerase such as Taq polymerase, and the polymerase amplifies the cDNA region between the two primers.

B. Preparation of a Vector for VEGF-B Expression

After cloning, the cDNA or gene encoding a VEGF-B polypeptide or fragment thereof has been isolated, it is preferably inserted into an amplification and/or expression vector in order to increase the copy number of the gene and/or to express the polypeptide in a suitable host cell and/or to transform cells in a target organism (to express VEGF-B in vivo). Numerous commercially available vectors are suitable, though "custom made" vectors may be used as well. The vector is selected to be functional in a particular host cell or host tissue (i.e., the vector is compatible with the host cell machinery such that amplification of the VEGF-B gene and/or expression of the gene can occur). The VEGF-B polypeptide or fragment thereof may be amplified/expressed in prokaryotic, yeast, insect (baculovirus systems) and/or eukaryotic host cells. Selection of the host cell will depend at least in part on whether the VEGF-B polypeptide or fragment thereof is to be glycosylated. If so, yeast, insect, or mammalian host cells are preferable; yeast cells will glycosylate the polypeptide if a glycosylation site is present on the VEGF-B amino acid sequence.

Typically, the vectors used in any of the host cells will a contain 5' flanking sequence and other regulatory elements as well such as enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Optionally, the vector may contain a "tag" sequence, i.e., an oligonucleotide sequence located at the 5' or 3' end of the VEGF-B coding sequence that encodes polyHis (such as hexaHis) or another small immunogenic sequence. This tag will be expressed along with the protein, and can serve as an affinity tag for purification of the VEGF-13 polypeptide from the host cell. Optionally, the tag can subsequently be removed from the purified VEGF-B polypeptide by various means such as using a selected peptidase for example.

The vector/expression construct may optionally contain elements such as a 5' flanking sequence, an origin of replication, a transcription termination sequence, a selectable marker sequence, a ribosome binding site, a signal sequence, and one or more intron sequences. The 5' flanking sequence may be homologous (i.e., from the same species and/or strain as the host cell), heterologous (i.e., from a species other than the host cell species or strain), hybrid (i.e., a combination of p5' flanking sequences from more than one source), synthetic, or it may be the native VEGF-B 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

An origin of replication is typically a part of commercial prokaryotic expression vectors, and aids in the amplification of the vector in a host cell. Amplification of the vector to a certain copy number can, in some cases, may be important for optimal expression of the VEGF-B polypeptide. If the vector of choice does not contain an origin of replication site, one may be chemically synthesized based on a known sequence, and ligated into the vector.

A transcription termination element is typically located 3' to the end of the VEGF-B polypeptide coding sequence and serves to terminate transcription of the VEGF-B polypeptide. Usually, the transcription termination element in prokaryotic cells is a G-C rich fragment followed by a poly T sequence. Such elements can be cloned from a library, purchased commercially as part of a vector, and readily synthesized.

Selectable marker genes encode proteins necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media.

A ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above.

All of the elements set forth above, as well as others useful in this invention, are well known to the skilled artisan and are described, for example, in Sambrook, et al., "Molecular Cloning: A Laboratory Manual," Cold Spring Harbor Laboratory Press, Cold Spring Harbor, N.Y. (1989) and Berger, et al., eds., "Guide To Molecular Cloning Techniques," Academic Press, Inc., San Diego, Calif. [1987].

For those embodiments of the invention where the recombinant VEGF-B is to be secreted, a signal sequence is preferably included to direct secretion from the cell where it is synthesized. Typically, the signal sequence is positioned in the coding region of the transgene towards or at the 5' end of the coding region. Many signal sequences have been identified, and any of them that are functional in the transgenic tissue may be used in conjunction with the transgene. Therefore, the signal sequence may be homologous or heterologous to the transgene, and may be homologous or heterologous to the transgenic mammal. Additionally, the signal sequence may be chemically synthesized using methods set forth above. However, for purposes herein, preferred signal sequences are those that occur naturally with the transgene (i.e., are homologous to the transgene).

In many cases, gene transcription is increased by the presence of one or more introns on the vector. The intron may be naturally-occurring within the transgene sequence, especially where the transgene is a full length or a fragment of a genomic DNA sequence. Where the intron is not naturally-occurring within the DNA sequence (as for most cDNAs), the intron(s) may be obtained from another source. The intron may be homologous or heterologous to the transgene and/or to the transgenic mammal. The position of the intron with respect to the promoter and the transgene is important, as the intron must be transcribed to be effective. As such, where the transgene is a cDNA sequence, the preferred position for the intron is 3' to the transcription start site, and 5' to the polyA transcription termination sequence. Preferably for cDNA transgenes, the intron will be located on one side or the other (i.e., 5' or 3') of the transgene sequence such that it does not interrupt the transgene sequence. Any intron from any source, including any viral, prokaryotic and eukaryotic (plant or animal) organisms, may be used to express VEGF-B, provided that it is compatible with the host cell(s) into which it is inserted. Also included herein are synthetic introns. Optionally, more than one intron may be used in the vector.

Preferred vectors for recombinant expression of VEGF-B protein are those that are compatible with bacterial, insect, and mammalian host cells. Such vectors include, inter alia, pCRII (Invitrogen Company, San Diego, Calif.), pBSII (Stratagene Company, La Jolla, Calif.), and pETL (BlueBacII; Invitrogen).

After the vector has been constructed and a VEGF-B nucleic acid has been inserted into the proper site of the vector, the completed vector may be inserted into a suitable host cell for amplification and/or VEGF-B polypeptide expression. The host cells typically used include, without limitation: Prokaryotic cells such as gram negative or gram positive cells, i.e., any strain of *E. coli, Bacillus, Streptomyces, Saccharomyces, Salmonella*, and the like; eukaryotic cells such as CHO (Chinese hamster ovary) cells, human kidney 293 cells, COS-7 cells; insect cells such as Sf4, Sf5, Sf9, and Sf21 and High 5 (all from the Invitrogen Company, San Diego, Calif.); and various yeast cells such as *Saccharomyces* and *Pichia*.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook, et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of VEGF-B polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as VEGFR-1 binding assays or cell stimulation assays.

C. Purification of VEGF-B Polypeptides

VEGF-B polypeptides are preferably expressed and purified as described in U.S. Pat. No. 6,331,301, incorporated herein by reference.

If the VEGF-B polypeptide is designed to be secreted from the host cells, the majority of the polypeptide will likely be found in the cell culture medium. If, however, the VEGF-B polypeptide is not secreted from the host cells, it will be present in the cytoplasm (for eukaryotic, gram positive bacteria, and insect host cells) or in the periplasm (for gram negative bacteria host cells).

For intracellular VEGF-B, the host cells are first disrupted mechanically or osmotically to release the cytoplasmic contents into a buffered solution. The polypeptide is then isolated from this solution.

Purification of VEGF-B polypeptide from solution can be accomplished using a variety of techniques. If the polypeptide has been synthesized such that it contains a tag such as Hexahistidine (VEGF-B/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing VEGF-B). For example, polyhistidine binds with great affinity and specificity to nickel, thus an affinity column of nickel (such as the Qiagen nickel columns) can be used for purification of VEGF-B/polyHis. (See, for example, Ausubel, et al, eds., "Current Protocols In Molecular Biology," Section 10.11.8, John Wiley & Sons, New York (1993)).

The strong affinity of VEGF-B for its receptor VEGFR-1 permits affinity purification of VEGF-B using an affinity matrix comprising VEGFR-1 extracellular domain. In addition, where the VEGF-B polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

VEGF-B polypeptide found in the periplasmic space of the bacteria or the cytoplasm of eukaryotic cells, the contents of the periplasm or cytoplasm, including inclusion bodies (bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the VEGF-B polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The VEGF-B polypeptide in its now soluble form can then be analyzed using gel electrophoresis, immunoprecipitation or the like. If it is desired to isolate the VEGF-B polypeptide, isolation may be accomplished using standard methods such as those set forth below and in Marston, et al., Meth. Enz., 182:264-275 (1990).

If VEGF-B polypeptide inclusion bodies are not formed to a significant degree in the periplasm of the host cell, the VEGF-B o polypeptide will be found primarily in the supernatant after centrifugation of the cell homogenate, and the VEGF-B polypeptide can be isolated from the supernatant using methods such as those set forth below.

In those situations where it is preferable to partially or completely isolate the VEGF-B polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

Anti-VEGF-B Therapeutic Compounds

Anti-VEGF-B therapies, as discussed below, include but are not limited to antibody, aptamer, antisense and interference RNA techniques and therapies. These agents are contemplated for numerous therapeutic contexts described herein, such as therapies directed to reducing lipid accumulation, and stimulating glucose metabolism and other parameters associated with metabolic syndrome in a mammalian subject.

A. Therapeutic Anti-VEGF-B Antibodies

Anti-VEGF-B antibodies as described in U.S. Pat. No. 6,331,301 are also contemplated for use in practicing the present invention. Such antibodies can be used for VEGF-B purification, or therapeutically where inhibition of VEGF-B is desired. See also WO 2005/087812, WO 2005/087808, U.S. Patent Application Publication No. 2005-0282233 and U.S. Patent Application Publication No. 2006-0030000, the disclosure of which are incorporated herein by reference in their entireties.

Polyclonal or monoclonal therapeutic anti-VEGF-B antibodies useful in practicing this invention may be prepared in laboratory animals or by recombinant DNA techniques using the following methods. Polyclonal antibodies to the VEGF-B molecule or a fragment thereof containing the target amino acid sequence generally are raised in animals by multiple subcutaneous (sc) or intraperitoneal (ip) injections of the VEGF-B molecule in combination with an adjuvant such as Freund's adjuvant (complete or incomplete). To enhance immunogenicity, it may be useful to first conjugate the VEGF-B molecule or a fragment containing the target amino acid sequence of to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOC_1$, or $R^1N{=}C{=}NR$, where R and $R^1$ are different alkyl groups. Alternatively, VEGF-B-immunogenic conjugates can be produced recombinantly as fusion proteins.

Animals are immunized against the immunogenic VEGF-B conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for anti-VEGF-B titer. Animals are boosted with antigen repeatedly until the titer plateaus. Preferably, the animal is boosted with the same VEGF-B molecule or fragment thereof as was used for the initial immunization, but conjugated to a different protein and/or through a different cross-linking agent. In addition, aggregating agents such as alum are used in the injections to enhance the immune response.

Monoclonal antibodies may be prepared by recovering spleen cells from immunized animals and immortalizing the cells in conventional fashion, e.g. by fusion with myeloma cells. The clones are then screened for those expressing the desired antibody. In some embodiments, the monoclonal antibody is specific for VEGF-B. In other embodiments, the monoclonal antibody cross-reacts with other VEGF/PDGF family members.

Preparation of antibodies using recombinant DNA methods, such as the phagemid display method, may be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Preferably, antibodies for administration to humans, although prepared in a laboratory animal such as a mouse, will be "humanized", or chimeric, i.e. made to be compatible with the human immune system such that a human patient will not develop an immune response to the antibody. Even more preferably, human antibodies which can now be prepared using methods such as those described for example, in Lonberg, et al., Nature Genetics, 7:13-21 (1994) are preferred for therapeutic administration to patients.

1. Humanization of Anti-VEGF-B Monoclonal Antibodies

VEGF-B-neutralizing antibodies comprise one class of therapeutics useful as VEGF-B antagonists. Following are protocols to improve the utility of anti-VEGF-B monoclonal antibodies as therapeutics in humans, by "humanizing" the monoclonal antibodies to improve their serum half-life and render them less immunogenic in human hosts (i.e., to prevent human antibody response to non-human anti-VEGF-B antibodies).

The principles of humanization have been described in the literature and are facilitated by the modular arrangement of antibody proteins. To minimize the possibility of binding complement, a humanized antibody of the $IgG_4$ isotype is preferred.

For example, a level of humanization is achieved by generating chimeric antibodies comprising the variable domains of non-human antibody proteins of interest, such as the anti-VEGF-B monoclonal antibodies described herein, with the constant domains of human antibody molecules. (See, e.g., Morrison and Oi, Adv. Immunol., 44:65-92 (1989)). The variable domains of VEGF-B neutralizing anti-VEGF-B antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarily determining regions ("CDR") of the non-human monoclonal antibody genes are cloned into human antibody sequences. (See, e.g., Jones, et al., Nature, 321:522-525 (1986); Riechmann, et al., Nature, 332:323-327 (1988); Verhoeyen, at al., Science, 239: 1534-36 (1988); and Tempest, at al., Bio/Technology, 9:266-71 (1991)). If necessary, the beta-sheet framework of the human antibody surrounding the CDR3 regions also is modified to more closely mirror the three dimensional structure of the antigen-binding domain of the original monoclonal antibody. (See, Kettleborough, et al., Protein Engin., 4:773-783 (1991); and Foote, et al., J. Mol. Biol., 224:487-499 (1992)).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, Molecular 28(4/5):489-98 (1991).

The foregoing approaches are employed using VEGF-B-neutralizing anti-VEGF-B monoclonal antibodies and the hybridomas that produce them to generate humanized VEGF-B-neutralizing antibodies useful as therapeutics to treat or palliate conditions wherein VEGF-B expression is detrimental.

2. Human VEGF-B-Neutralizing Antibodies from Phage Display

Human VEGF-B-neutralizing antibodies are generated by phage display techniques such as those described in Aujame, at al., Human Antibodies, 8(4):155-168 (1997); Hoogenboom, TIBTECH, 15:62-70 (1997); and Rader, at al., Curr. Opin. Biotechnol., 8:503-508 (1997), all of which are incorporated by reference. For example, antibody variable regions in the form of Fab fragments or linked single chain Fv fragments are fused to the amino terminus of filamentous phage minor coat protein pill. Expression of the fusion protein and incorporation thereof into the mature phage coat results in phage particles that present an antibody on their surface and contain the genetic material encoding the antibody. A phage library comprising such constructs is expressed in bacteria, and the library is panned (screened) for VEGF-B-specific phage-antibodies using labeled or immobilized VEGF-B respectively as antigen-probe.

3. Human VEGF-B-Neutralizing Antibodies from Transgenic Mice

Human VEGF-B-neutralizing antibodies are generated in transgenic mice essentially as described in Bruggemann and Neuberger, Immunol. Today, 17(8):391-97 (1996) and Bruggemann and Taussig, Curr. Opin. Biotechnol., 8:455-58 (1997). Transgenic mice carrying human V-gene segments in germline configuration and that express these transgenes in their lymphoid tissue are immunized with VEGF-B composition using conventional immunization protocols. Hybridomas are generated using B cells from the immunized mice using conventional protocols and screened to identify hybridomas secreting anti-VEGF-B human antibodies (e.g., as described above).

4. Bispecific Antibodies

Bispecific antibodies that specifically bind to one protein (e.g., VEGF-B) and that specifically bind to other antigens relevant to pathology and/or treatment are produced, isolated, and tested using standard procedures that have been described in the literature. See, e.g., Pluckthun & Pack, Immunotechnology, 3:83-105 (1997); Carter, et al., 3. Hematotherapy, 4: 463-470 (1995); Renner & Pfreundschuh, Immunological Reviews, 1995, No. 145, pp. 179-209; Pfreundschuh U.S. Pat. No. 5,643,759; Segal, et al., J. Hematotherapy, 4: 377-382 (1995); Segal, et al., Immunobiology, 185: 390-402 (1992); and Bolhuis, et al., Cancer Immunol. Immunother., 34: 1-8 (1991), all of which are incorporated herein by reference in their entireties. For example, in one embodiment, bispecific antibodies that specifically bind to VEGF-B and specifically bind to VEGF-A or P1GF is contemplated.

B. Anti-VEGFR-1 Antibodies

Anti-VEGFR-1 antibodies that inhibit binding to and activation of VEGF-B are also contemplated as another inhibitor of VEGF-B that is useful for practicing the invention. Suitable antibodies include Avastin, in mAb 6.12, and MF1. Likewise, monoclonal, polyclonal, human, humanized and bispecific antibodies are also contemplated.

C. VEGFR-1 Antagonists

VEGFR-1 antagonists that inhibit binding to and activation of VEGF-B are also contemplated as another inhibitor of VEGF-B that is useful for practicing the invention. Suitable VEGFR-1 antagonists include Sutent, SU5416, and those disclosed in WO 2005/087808 and US Patent Publication No. 2006-0030000, the disclosure of which are incorporated herein by reference in their entireties.

D. Anti-VEGF-B Aptamers

Recent advances in the field of combinatorial sciences have identified short polymer sequences with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, ligands can be created which bind to VEGF-B. Curiously, in each case, a loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compare to linear peptide phage display results. Thus, sufficient evidence has been generated to suggest that high affinity ligands can be created and identified by combinatorial molecular evolution techniques. For the present invention, molecular evolution techniques can be used to isolate ligands specific for VEGF-B, to be used in a manner analogous to that discussed above for anti-VEGF-B antibodies. For more on aptamers, see generally, Gold, L., Singer, B., He, Y. Y., Brody. E., "Aptamers As Therapeutic And Diagnostic Agents," J. Biotechnol. 74:5-13 (2000).

E. Anti-Sense Molecules and Therapy

Another class of VEGF-B inhibitors useful in the present invention is isolated antisense nucleic acid molecules that can hybridize to, or are complementary to, the nucleic acid molecule comprising the VEGF-B nucleotide sequence, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). (See, for example, Uhlmann, et al. Antisense oligonucleotides: A new therapeutic principle. Chemical Reviews 1990, 90: 543-584; Crooke, et al. "Antisense Research and Applications", CRC Press (1993); Mesmaekar, et al. "Antisense oligonucleotides," Acc. Chem. Res. 1995, 28: 366-374; Stein. "The experimental use of antisense oligonucleotides: a guide for the perplexed." J. Clin. Invest. 2001, 108, 641-644, and U.S. Pat. Nos. 6,117,992; 6,127,121; 6,235,887; 6,232,463; 6,579,704; 5,596,091; 6,031,086 and 6,117,992, the disclosures of which are incorporated herein by reference in their entireties). In specific aspects, antisense nucleic acid molecules are provided that comprise a sequence complementary to at least about 10, 25, 50, 100, 250 or 500 nucleotides or an entire VEGF-B coding strand, or to only a portion thereof. Nucleic acid molecules encoding fragments, homologs, derivatives and analogs of VEGF-B antisense nucleic acids complementary to a VEGF-B nucleic acid sequence are additionally provided.

In one embodiment, an antisense nucleic acid molecule is antisense to a "coding region" of the coding strand of a nucleotide sequence encoding a VEGF-B protein. The term "coding region" refers to the region of the nucleotide sequence comprising codons that are translated into amino add residues. In another embodiment, the antisense nucleic acid molecule is antisense to a "conceding region" of the coding strand of a nucleotide sequence encoding the VEGF-B protein. The term "conceding region" refers to 5' and 3' sequences that flank the coding region and that are not translated into amino acids (i.e., also referred to as 5' and 3' untranslated regions).

Given the coding strand sequences encoding the VEGF-B protein disclosed herein, antisense nucleic acids of the invention can be designed according to the rules of Watson and Crick or Hoogsteen base pairing. The antisense nucleic acid molecule can be complementary to the entire coding region of VEGF-B mRNA, but more preferably is an oligonucleotide that is antisense to only a portion of the coding or noncoding region of VEGF-B mRNA. For example, the antisense oligonucleotide can be complementary to the region surrounding the translation start site of VEGF-B mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following section).

The antisense nucleic acid molecules of the invention are typically administered to a subject or generated in situ such that they hybridize with or bind to cellular mRNA and/or genomic DNA encoding VEGF-B to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., Nucl. Acids Res., 15:6625-6641 (1987). The antisense nucleic acid molecule can also comprise a 2'-o-methylribonucleotide (see, e.g., Inoue, et al. Nucl. Acids Res., 15:6131-6148 (1987)) or a chimeric RNA-DNA analogue (see, e.g., Inoue, et al., FEBS Lett., 215:327-330 (1987)).

Production and delivery of antisense molecules are facilitated by providing a vector comprising an anti-sense nucleotide sequence complementary to at least a part of the VEGF-B DNA sequence. According to a yet further aspect of the invention such a vector comprising an anti-sense sequence may be used to inhibit, or at least mitigate, VEGF-B expression. The use of a vector of this type to inhibit VEGF-B expression is favored in instances where VEGF-B expression is associated with a particular disease state.

F. Anti-VEGF-B RNA Interference

Use of RNA Interference to inactivate or modulate VEGF-B expression is also contemplated as part of this invention. RNA interference is described in U.S. Patent Appl. No. 2002-0162126, and Hannon, G., J. Nature, 11:418:244-51 (2002). "RNA interference," "post-transcriptional gene silencing," "quelling"—these terms have all been used to describe similar effects that result from the over-expression or misexpression of transgenes, or from the deliberate introduction of double-stranded RNA into cells (reviewed in Fire, A., Trends Genet 15:358-363 (1999); Sharp, P. A., Genes Dev., 13:139-141 (1999); Hunter, C., Curr. Biol., 9:R440-R442 (1999); Baulcombe, D. C., Curr. Biol. 9:R599-R601 (1999); Vaucheret, et al. Plant J. 16:651-659 (1998), all incorporated by reference. RNA interference, commonly referred to as RNAi, offers a way of specifically and potently inactivating a cloned gene.

RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, RNAi may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNase L, a non-specific enzyme that targets all mRNAs. The nonspecific pathway may represents a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al. (1975) J. Biol. Chem. 250: 409-17; Manche et al. (1992) Mol. Cell Biol. 12: 5239-48; Minks et al. (1979) J. Biol. Chem. 254: 10180-3; and Elbashir et al. (2001) Nature 411: 494-8). RNAi has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass (2001) Nature 411: 428-9). In mammalian cells, siRNAs are effective at concentrations that are several orders of magnitude below the concentrations typically used in antisense experiments (Elbashir et al. (2001) Nature 411: 494-8).

The double stranded oligonucleotides used to affect RNAi are preferably less than 30 base pairs in length and, more preferably, comprise about 25, 24, 23, 22, 21, 20, 19, 18 or 17 base. pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the alt. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a VEGF-B nucleic acid.

Similar to the antisense molecules discussed above, RNAi suitable for the present invention may also be made VEGF-B isoform-specific.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which that represent preferred segments of the mRNA to target for silencing RNAi, ribozyme or antisense technologies. Accordingly, preferred segments of the mRNA target can be identified for design of the RNAi mediating dsRNA oligonucleotides.

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141: 863-74). The effectiveness of the RNAi may be assessed by any of a number of assays following introduction of the dsRNAs. These include Western blot analysis using antibodies which recognize the VEGF-B gene product following sufficient time for turnover of the endogenous pool after new protein synthesis is repressed, reverse transcriptase polymerase chain reaction and Northern blot analysis to determine the level of existing VEGF-B target mRNA.

Further compositions, methods and applications of RNAi technology are provided in U.S. Pat. Nos. 6,278,039, 5,723, 750 and 5,244,805, which are incorporated herein by reference.

Therapeutic Uses for the Anti-VEGF-B Compounds

The present invention provides for both prophylactic and therapeutic methods of treating subjects (e.g., humans or other animals). In one aspect, the invention provides preventing or treating a disease or a disorder in a subject through prophylactic or therapeutic methods.

Administration of a therapeutic agent in a prophylactic method can occur prior to the manifestation of symptoms of an undesired disease or disorder, such that the disease or disorder is prevented or, alternatively, delayed in its progression.

As used herein, the terms "treating" or "treatment" includes the application or administration of a therapeutic agent to a subject who is afflicted with a disease, a symptom of disease or a predisposition toward an undesired disease or disorder, with the goal of curing, healing, alleviating, relieving, altering, remedying, ameliorating, improving or affecting the disease, the symptoms of disease or disorder or the predisposition toward the disease or disorder, or delaying its onset or progression.

The methods and anti-VEGF-B compounds of the present invention are useful for treating any mammalian subject that has been diagnosed with or is at risk of having a metabolic disorder. A subject in whom the development of a metabolic disorder (e.g., diabetes, obesity, metabolic syndrome, etc.) is being prevented may or may not have received such a diagnosis. One in the art will understand that the subjects may have been subjected to standard tests or may have been identified, without examination, as one at high risk due to the presence of one or more risk factors, which are described below.

Diagnosis of metabolic disorders may be performed using any standard method known in the art, such as those described herein. Methods for diagnosing diabetes are described, for example, in U.S. Pat. No. 6,537,806, incorporated herein by reference. Diabetes may be diagnosed and monitored using, for example, urine tests (urinalysis) that measure glucose and ketone levels (products of the breakdown of fat); tests that measure the levels of glucose in blood; glucose tolerance tests; and assays that detect molecular markers characteristic of a metabolic disorder in a biological sample (e.g., blood, serum, or urine) collected from the mammal (e.g., measurements of Hemoglobin A1c (HbA1c) levels in the case of diabetes).

Patients may be diagnosed as being at risk or as having diabetes if a random plasma glucose test (taken at any time of the day) indicates a value of 200 mg/dL or more, if a fasting plasma glucose test indicates a value of 126 mg/dL or more (after 8 hours), or if an oral glucose tolerance test (OGTT) indicates a plasma glucose value of 200 mg/dL or more in a blood sample taken two hours after a person has consumed a drink containing 75 grams of glucose dissolved in water. The OGTT measures plasma glucose at timed intervals over a 3-hour period. Desirably, the level of plasma glucose in a diabetic patient that has been treated according to the invention ranges between 160 to 60 mg/dL, between 150 to 70 mg/dL, between 140 to 70 mg/dL, between 135 to 80 mg/dL, and preferably between 120 to 80 mg/dL.

Optionally, a hemoglobin A1c (HbA1c) test, which assesses the average blood glucose levels during the previous two and three months, may be employed. A person without diabetes typically has an HbA1c value that ranges between 4% and 6%. For every 1% increase in HbA1c, blood glucose levels increases by approximately 30 mg/dL and the risk of complications increases. Preferably, the HbA1c value of a subject being treated according to the present invention is reduced to less than 9%, less than 7%, less than 6%, and most preferably to around 5%. Thus, the HbA1c levels of the subject being treated are preferably lowered by 10%, 20%, 30%, 40%, 50%, or more relative to such levels prior to treatment.

Gestational diabetes is typically diagnosed based on plasma glucose values measured during the OGTT. Since glucose levels are normally lower during pregnancy, the threshold values for the diagnosis of diabetes in pregnancy are lower than in the same person prior to pregnancy. If a woman has two plasma glucose readings that meet or exceed any of the following numbers, she has gestational diabetes: a fasting plasma glucose level of 95 mg/dL, a 1-hour level of 180 mg/dL, a 2-hour level of 155 mg/dL, or a 3-hour level of 140 mg/dL.

Ketone testing may also be employed to diagnose type I diabetes. Because ketones build up in the blood when there is not enough insulin, they eventually accumulate in the urine. High levels of blood ketones may result in a serious condition called ketoacidosis.

The use of any of the above tests or any other tests known in the art may be used to monitor the efficacy of the present treatment. Since the measurements of hemoglobin A1c (HbA1c) levels is an indication of average blood glucose during the previous two to three months, this test may be used to monitor a patient's response to diabetes treatment.

Abnormalities of fatty-acid metabolism are increasingly recognized as key components of the pathogenesis of the metabolic syndrome and type-II diabetes (McGarry, J. Science, 258:765-770, 1992). Fat-feeding and raised levels of circulating FFAa are clearly sufficient to induce peripheral and hepatic insulin resistance. Accumulation of lipids inside muscle cells (Krssak et al., Diabetologin. 42:113-116, 1999) and specific increases in muscle long-chain fatty-acyl-CoA content (Ruderman et al., Am. Physiol., 276; E1-E18, 1999) have been implicated in causing insulin resistance. In additional, lipid accumulation within pancreatic islets has been proposed to impair insulin secretion (Unger, R., Diabetes, 44:863-870, 1993). Thus, it is contemplated that the anti-VEGF-B compounds of the invention can be used to treat or prevent insulin resistance associated with diabetes, obesity and metabolic syndrome or symptoms associated therewith.

One category of subjects to be treated according to the invention are subjects with metabolic syndrome. Metabolic syndrome (also referred to as syndrome X) is a cluster of risk factors that is responsible for increased cardiovascular morbidity and mortality. Metabolic syndrome is typically characterized by a group of metabolic risk factors that include 1) central obesity; 2) atherogenic dyslipidemia (blood fat disorders comprising mainly high triglycerides ("TG") and low HDL-cholesterol (interchangeably referred to herein as "HDL") that foster plaque buildups in artery walls); 3) raised blood pressure; 4) insulin resistance or glucose intolerance (the body can't properly use insulin or blood sugar); 5) prothrombotic state (e.g., high fibrinogen or plasminogen activator inhibitor in the blood); and 6) a proinflammatory state (e.g., elevated high-sensitivity C-reactive protein in the blood). The National Cholesterol Education Program (NCEP) Adult Treatment Panel (ATP) III guidelines define metabolic syndrome by the following five clinical parameters: a) a waist circumference greater than 102 cm for men, and greater than 88 cm for women; b) a triglyceride level greater than 150 mg/dl; c) an HDL-cholesterol less than 40 mg/dl for men, and less than 50 mg/dl for women; d) a blood pressure greater than or equal to 130/85 mmHG; and e) a fasting glucose greater than 110 mg/dl.

Another category of subjects to be treated according to the invention are subjects with dyslipidemias. As used herein, dyslipidemia is an abnormal serum, plasma, or blood lipid profile in a subject. An abnormal lipid profile may be characterized by total cholesterol, low density lipoprotein (LDL)-cholesterol, triglyceride, apolipoprotein (apo)-B or Lp(a) levels above the $90^{th}$ percentile for the general population or high density lipoprotein (HDL)-cholesterol or apo A-1 levels below the $10^{th}$ percentile for the general population. Dyslipidemia can include hypercholesterolemia and/or hypertriglyceridemia. Hypercholesterolemic human subjects and hypertriglyceridemic human subjects are associated with increased incidence of cardiovascular disorders. A hypercholesterolemic subject has an LDL cholesterol level of >160 mg/dL, or >130 mg/dL and at least two risk factors selected from the group consisting of male gender, family history of premature coronary heart disease, cigarette smoking, hypertension, low HDL (<35 mg/dL), diabetes mellitus, hyperinsulinemia, abdominal obesity, high lipoprotein, and personal history of a cardiovascular event. A hypertriglyceridemic human subject has a triglyceride (TG) level of >200 mg/dL.

Dyslipidemias encompassed by this invention include dyslipidemias caused by single gene defects, dyslipidemias that are multifactorial or polygenic in origin, as well as dyslipidemias that are secondary to other disease states or secondary to pharmacological agents. Examples of genetic dyslipidemias include Familial Hypercholesterolemia, Familial Defective Apo B 100, Familial Hypertriglyceridemia, Familial Apoprotein CII deficiency, Hepatic Lipase Deficiency, Familial Combined Hyperlipidemia, Dysbetalipoproteinemia, and Familial Lipoprotein Lipase Deficiency.

Another category of subjects to be treated according to the invention are subjects with cardiovascular disorders. "Cardiovascular disorder", as used herein, includes elevated blood pressure, atherosclerosis, heart failure or a cardiovascular event such as acute coronary syndrome, myocardial infarction, myocardial ischemia, chronic stable angina pectoris, unstable angina pectoris, angioplasty, stroke, transient ischemic attack, claudication(s), or vascular occlusion(s).

Risk factors for a cardiovascular disorder include dyslipidemia, obesity, diabetes mellitus, pre-hypertension, elevated level(s) of a marker of systemic inflammation, age, a family history of cardiovascular disorders, and cigarette smoking.

The degree of risk of a cardiovascular disorder or a cardiovascular event depends on the multitude and the severity or the magnitude of the risk factors demonstrated by the subject. Risk charts and prediction algorithms are available for assessing the risk of cardiovascular disorders and cardiovascular events in a human subject based on the presence and severity of risk factors.

The anti-VEGF-B compounds of the invention can be administered alone or in combination with one or more further pharmacologically active substances which have, for example, favorable effects on metabolic disturbances or disorders frequently associated therewith. Examples of such medicaments are medicaments which lower blood glucose, anti-diabetics, active ingredients for the treatment of dyslipidemias, anti-atherosclerotic medicaments, anti-obesity agents, anti-inflammatory active ingredients, active ingredients for the treatment of malignant tumors, anti-thrombotic active ingredients, active ingredients for the treatment of high blood pressure, active ingredients for the treatment of heart failure and active ingredients for the treatment and/or prevention of complications caused by diabetes or associated with diabetes.

Furthermore, the anti-VEGF-B compounds may be administered in combination with one or more anti-hypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, alatriopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Any suitable combination of the compounds according to the invention with one or more of the above-mentioned anti-VEGF-B compounds and optionally one or more further pharmacologically active substances are considered to be within the scope of the present invention.

At present, therapy for diabetes (i.e., type II diabetes) relies mainly on several approaches intended to reduce the hyperglycaemia itself: sulphonylureas (and related insulin secretagogues), which increase insulin release from pancreatic islets; metformin, which acts to reduce hepatic glucose production; peroxisome proliferators-activated receptor-γ (PPAR-γ) agonists (thiazolidinediones), which enhance insulin action; α-glucosidase inhibitors, which interfere with gut glucose absorption; and insulin itself, which suppresses glucose production and augments glucose utilization.

The one or more further pharmacologically active substances can be combined with the anti-VEGF-B compounds of the invention in particular for a synergistic improvement in the effect. Administration oldie active ingredient combination can take place either by separate administration of the active ingredients to the patient or in the form of combination products.

Therapeutic Uses for the VEGF-B Polynucleotides

In one embodiment, the therapeutic effects of VEGF-B on improving tissue or organ transplantation in a mammalian subject are achieved by administration of VEGF-B encoding polynucleotides (including vectors comprising such polynucleotides) to a subject that will benefit from the VEGF-B.

In a related embodiment, it is contemplated that the VEGF-B polynucleotides of the invention are administered in conjunction with other VEGF/PDGF family members. To date a number of PDGF/VEGF family members have been identified. These include PDGF-A (see e.g., GenBank Acc. No. X06374), PDGF-B (see e.g., GenBank Ace. No. M12783), PDGF-C (Intl. Publ. No. WO 00/18212), PDGF-D (Intl. Publ. No. WO 00/027879), VEGF (also known as VEGF-A or by particular isoform), Placenta growth factor, P1GF (U.S. Pat. No. 5,919,899), VEGF-C, (U.S. Pat. No. 6,221,839 and WO 98/33917), VEGF-D (also known as c-fos-induced growth factor (FIGF) (U.S. Pat. No. 6,235,713, Intl. Publ. No. WO98/07832), VEGF-E (also known as NZ7 VEGF or OV NZ7; Intl. Publ. No. WO00/025805 and U.S. Patent Publ. No. 2003/0113870), NZ2 VEGF (also known as OV NZ2; see e.g., GenBank Ace. No. S67520), D1701 VEGF-like protein (see e.g., GenBank Acc. No. AF106020; Meyer at al., EMBO J 18:363-374), and NZ10 VEGF-like protein (described in Intl. Patent Application PCT/US99/25869) [Stacker and Achen, Growth Factors 17:1-11 (1999); Neufeld at al., FASEB J 13:9-22 (1999); Ferrara, J Mol Med 77:527-543 (1999)].

In another embodiment, the therapeutic effects of VEGF-B can be achieved by administering VEGF-B encoding polynucleotides (including vectors comprising such polynucleotides) to subjects having cachexia and other wasting diseases. Body weight disorders include one or more "wasting" disorders (e.g., wasting syndrome, cachexia, sarcopenia) which cause undesirable and unhealthy loss of weight or loss of body cell mass. In the elderly as well as in cancer and AIDS patients, wasting diseases can result in undesired loss of body weight. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease. Wasting disease is sometimes also referred to as cachexia, and is generally recognized as a metabolic and, sometimes, an eating disorder. Cachexia may additionally be characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Roubenoff R., J. Nutr. 129(1 S Suppl.):256S-259S (1999)). Sarcopenia, yet another such disorder which can affect the aging individual, is typically characterized by loss of muscle mass. End stage wasting disease as described above can develop in individuals suffering from either cachexia or sarcopenia.

In yet another embodiment, it is contemplated that the VEGF-B polynucleotides (including vectors comprising such polynucleotides) and polypeptides used for the treatment or prophylaxis of cachexia are administered in combination with other drugs or agents. These other drugs and agents may include agents that induce weight gain, including corticosteroids and progestational agents. In a preferred embodiment of the invention, the VEGF-B polynucleotides and polypeptides of the invention are used in combination with a therapeutically effective amount of a second weight gain pharmaceutical agent.

In a related embodiment, the second compound useful for the treatment or prophylaxis of cachexia are preferably selected from but not limited to the group consisting of ADP-ribose-polymerase inhibitors, ADP-ribose-transferase inhibitors, NADase inhibitors, nicotinamide benzamide, theophylline, thymine and analogs thereof; omega-3 fatty acids such as alpha-linolenic acid, stearidonic acid, eicosapentaenoic acid (EPA), docosapentaenoic acid, docosahexaenoic acid or mixtures thereof; branched-chain amino acids valine, leucine, isoleucine or mixtures thereof, with or without reduced levels of tryptophan and 5-hydroxytryptophan; antioxidants selected from the group comprising beta-carotene, vitamin C, vitamin E, selenium, or mixtures thereof; L-glutamine, vitamin A, vitamin C, vitamin E, and selenium; Azaftig; quinine derivatives including 3,5,6-trimethyl-2-(3-pyridyl)methyl-1,4-benzoquinone hydrochloride; interleukin 2; benzaldehyde; 4,6-O-benzylidene-D-glucose; friedelan-3-one; hydrazine sulfate; medroxyprogesterone acetate; beta 2-adrenoceptor agonists; corticosteroids such as dexamethasone; Vitor™; Pro-Stat™; megestrol acetate (Megace™); dronabinol (Marinol™); magestrol acetate (Megace™); thalidomide (Thalidomid™); fluoxymesterone (Halotestin™); pentoxifylline (Trental™); cyproheptadine (Periactin™); metoclopramide (Reglan™); somatropin (Serostim™); total parenteral nutrition; or other MC4-R antagonists.

In yet another embodiment, the therapeutic effects of VEGF-B on neurodegenerative disorders are achieved by administration of VEGF-B encoding polynucleotides (including vectors comprising such polynucleotides) to a subject that will benefit from the VEGF-B. Neurodegenerative disorders are characterized by a progressive degeneration (i.e., nerve cell dysfunction and death) of specific brain regions, resulting in weakened motor function, which may lead to dampened cognitive skills and dementia. Examples of neurodegenerative disorders include but are not limited to Alzheimer's disease, Parkinson's disease, ALS and motor neuron disease.

Alzheimer's disease is diagnosed as a progressive forgetfulness leading to dementia. The AD brain demonstrates diffuse cerebral atrophy with enlarged ventricles, resulting from neuronal loss. In general, neurons in the hippocampal region are primarily involved in the pathology of AD.

Parkinson's Disease is characterized by tremors and reduced motor neuron function, rigidity, and akinesia. These neurologic signs are due to malfunction of the major efferent projection of the substantia nigra, i.e., the nigrostriatal tract. The cell bodies of neurons in the dopaminergic system are the primary cells involved in PD progression. Examples of primary parkinsonian syndromes include Parkinson's disease (PD), progressive supranuclear palsy (PSP), and striatonigral degeneration (SND), which is included with olivopontocerebellar degeneration (OPCD) and Shy Drager syndrome (SDS) in a syndrome known as multiple system atrophy (MSA).

Amyotrophic lateral sclerosis (ALS), often referred to as "Lou Gehrig's disease," is a progressive neurodegenerative disease that attacks motor neurons in the brain and spinal cord. The progressive degeneration of the motor neurons in ALS eventually leads to their death, reducing the ability of the brain to initiate and control muscle movement.

Huntington's disease (HD), although a genetically heritable disease, results in the degeneration of neurons in the striatal medium spiny GABAergic neurons (Hickey at al., *Prog Neuropsychopharmacol Biol Psychiatry.* 27:255-65, 2003). This degeneration causes uncontrolled movements, loss of intellectual faculties, and emotional disturbance.

Cerebral palsy (CP) is another condition that may be treated by the method of the invention. CP syndromes are a group of related motor disorders with originating usually from either developmental abnormalities or perinatal or postnatal central nervous system (CNS) disorder damage occurring before age 5. CP is characterized by impaired voluntary movement.

A patient suffering from any of the above disorders can be treated at the earliest signs of disease symptoms, such as impaired motor function or impaired cognitive function, in order to halt the progression of neurodegeneration.

It is also contemplated by the invention that administration of VEGF-B in combination with a neurotherapeutic agent commonly used to treat neuropathologies will create a synergism of the two treatments, thereby causing marked improvement in patients receiving the combination therapy as compared to individuals receiving only a single therapy.

Neurodegenerative disorders are treatable by several classes of neurotherapeutics. Therapeutics include, but are not limited to the following drugs: secretin, amantadine hydrochloride, risperidone, fluvoxamine, clonidine, amisulpride, bromocriptine clomipramine and desipramine.

Neurotherapeutics commonly used to treat Alzheimer's disease include tacrine (Cognex), donepezil (Aricept), rivastigmine (Exelon), or galantamine (Reminyl) which may help prevent some symptoms from becoming worse for a limited time. Also, some medicines may help control behavioral symptoms of AD such as sleeplessness, agitation, wandering, anxiety, and depression. Additional therapies for AD are anti-inflammatory drugs such as non-steroidal anti-inflammatory drugs (NSAIDs), e.g. COX-2 inhibitors (Celebrex) and naproxen sodium. Other anti-inflammatory agents also used are salicylates, steroids, receptor site blockers, or inhibitors of complement activation.

Pramipexole (mirapex) and levodopa are effective medications to treat motor symptoms of early Parkinson disease (PD). In vitro studies and animal studies suggest that pramipexole may protect and that levodopa may either protect or damage dopamine neurons. Neuroimaging offers the potential of an objective biomarker of dopamine neuron degeneration in PD patients. Coenzyme Q10, a neurotransmitter that is expressed at low levels in Parkinson's patients, is also used for treatment of PD. Levodopa can be combined with another drug such as carbidopa to aid in relieving the side effects of L-dopa. Other medications used to treat Parkinson's disease, either as solo agents or in combination, are Sinemet, Selegiline, (marketed as Eldepryl) may offer some relief from early Parkinson symptoms. Amantadine (Symmetrel) is an anti-viral drug that also provides an anti-Parkinson effect, and is frequently used to widen the "therapeutic window" for Levodopa when used in combination with Sinemet Benadryl, Artane, and Cogentin are brand names for anticholinergic agents that may be prescribed to treat tremors. Anticholinergics block the action of acetylcholine in the neuromuscular junction, thereby rebalancing it in relation to dopamine and reducing rigidity and tremor. While effective, these drugs can have side effects such as dry mouth, blurred vision, urinary retention and constipation which limits their use in older adults.

Ropinirole (Requip), Pramipexole (Mirapex), Bromocriptine (Parlodel) and Pergolide (Permax) are dopamine agonists. These drugs enter the brain directly at the dopamine receptor sites, and are often prescribed in conjunction with Sinemet to prolong the duration of action of each dose of levodopa. They may also reduce levodopa-induced involuntary movements called "dyskinesias". The physician slowly titrates a dopamine agonist to a therapeutic level, then gradually decreases the levodopa dose to minimize dyskinesias. Apomorphine is a dopamine agonist often given as a continuous subcutaneous infusion or as a subcutaneous injection.

Tolcapone (Tasman) and Entacapone, are COMT (catechol-0-methyl-transterase) inhibitors. When COMT activity is blocked, dopamine remains in the brain for a longer period of time. Their mechanism of action is totally different than that of dopamine agonists.

Rilutek®, Myotrophin®, Coenzyme Q, Topiramate, Xaliproden and Oxandrolone are exemplary agents used in the treatment of ALS.

It is contemplated that treatment with VEGF-B, either before, after or simultaneously with any of the above neurotherapeutics will enhance the effect of the neurotherapeutic agent, thereby reducing the amount of agent required by an individual and reducing unwanted side effects produced by multiple or large doses of neurotherapeutic.

In yet another embodiment, VEGF-B encoding polynucleotides (including vectors comprising such polynucleotides) can be administered in conjunction with a PDGF-CC inhibitor. Co-owned, co-pending U.S. Patent Application Ser. No. 60/792,318, incorporated herein by reference, reports that administration of PDGF-CC mediates neuronal damage as a result of cerebral edema. Cerebral edema is a non-specific reaction to injury that occurs in a wide variety of CNS diseases, including head trauma, subarachnoid hemorrhage and ischemic stroke. Thus, the administration of PDGF-CC in conjunction with the VEGF-B encoding polypeptides in the neurodegenerative and cardiovascular embodiments described herein is specifically contemplated.

In another embodiment, the therapeutic effects of VEGF-B can be achieved by administering VEGF-B encoding polynucleotides (including vectors comprising such polynucleotides) to mammalian subjects for preventing wrinkles and aberrant hair growth is also contemplated. Moulson et al., (Proc. Natl. Acad. Sci., 100:5274-5279, 2003) report that FATP4 has a role in early development, specifically in the developments of the epithelial barrier. Mice with an FATP4 mutation did not fully develop this skin barrier and also failed to produce wrinkles.

For the above-described embodiments, an exemplary expression construct comprises a virus or engineered construct derived from a viral genome. The expression construct generally comprises a nucleic acid encoding the gene to be expressed and also additional regulatory regions that will effect the expression of the gene in the cell to which it is administered. Such regulatory regions include for example promoters, enhancers, polyadenylation signals and the like.

It is now widely recognized that DNA may be introduced into a cell using a variety of viral vectors. In such embodiments, expression constructs comprising viral vectors containing the genes of interest may be adenoviral (see, for example, U.S. Pat. No. 5,824,544; U.S. Pat. No. 5,707,618; U.S. Pat. No. 5,693,509; U.S. Pat. No. 5,670,488; U.S. Pat. No. 5,585,362; each incorporated herein by reference), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719 each incorporated herein by reference), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479 each incorporated herein by reference), an adenoviral-adenoassociated viral hybrid (see, for example, U.S. Pat. No. 5,856,152 incorporated herein by reference) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688 each incorporated herein by reference) vector. For many applications, replication-deficient strains of viruses are preferred.

In other embodiments, non-viral delivery is contemplated. These include calcium phosphate precipitation (Graham and Van Der Eb, Virology, 52:456-467 (1973); Chen and Okayama, Mol. Cell Biol., 7:2745-2752, (1987); Rippe, at al., Mol. Cell Biol., 10:689-695 (1990)), DEAE-dextran (Gopal, Mol. Cell Biol., 5:1188-1190 (1985)), electroporation (Tur-Kaspa, at al., Mol. Cell Biol., 6:716-718, (1986); Potter, at al., Proc. Nat. Acad. Sci. USA, 81:7161-7165, (1984)), direct microinjection (Harland and Weintraub, J. Cell Biol., 101: 10944099 (1985)), DNA-loaded liposomes (Nicolau and Sene, Biochim. Biophys. Acta, 721:185-190 (1982); Fraley, et al., Proc. Natl. Acad. Sci. USA, 76:3348-3352 (1979); Feigner, Sci. Am., 276(6):102-6 (1997); Feigner, Hum. Gene Ther., 7(15):1791-3, (1996)), cell sonication (Fechheimer, at al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990)), and receptor-mediated transfection (Wu and Wu, J. Biol. Chem., 262:4429-4432 (1987); Wu and Wu, Biochemistry, 27:887-892 (1988); Wu and Wu, Adv. Drug Delivery Rev., 12:159-167 (1993)).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., Science, 275(5301):810-4, (1997)). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., Science, 243:375-378 (1989)). In other embodiments, the liposome may be complexed or employed in conjunction with nuclear nonhistone chromosomal proteins (HMG-1) (Kato, et al., J. Biol. Chem., 266:3361-3364 (1991)). In yet further embodiments, the liposome may be complexed or employed in conjunction with both HVJ and HMG-1. In that such expression constructs have been successfully employed in transfer and expression of nucleic acid in vitro and in viva, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

Receptor-mediated gene targeting vehicles generally consist of two components: a cell receptor-specific ligand and a DNA-binding agent. Several Uganda have been used for receptor-mediated gene transfer. The most extensively characterized ligands are asialoorosomucoid (ASOR) (Wu and Wu (1987), supra) and transferrin (Wagner, et al., Proc. Nat'l. Acad. Sci. USA, 87(9):3410-3414 (1990)). Recently, a synthetic neoglycoprotein, which recognizes the same receptor as ASOR, has been used as a gene delivery vehicle (Ferkol, et al., *FASEB. J.*, 7:1081-1091 (1993); Perales, at al., *Proc. Natl. Acad. Sci., USA* 91:4086-4090 (1994)) and epidermal growth factor (EGF) has also been used to deliver genes to squamous carcinoma cells (Myers, EPO 0273085).

In other embodiments, the delivery vehicle may comprise a ligand and a liposome. For example, Nicolau, et al., *Methods Enzymol.*, 149:157-176 (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA*, 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA*, 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, at al, *Nature*, 327:70-73 (1987)). Several devices for accelerating small particles have been developed. One such device relies on a high voltage discharge to generate an electrical current, which in turn provides the motive force (Yang, et al., *Proc. Natl. Acad. Sci USA*, 87:9568-9572 (1990)). The microprojectiles used have consisted of biologically inert substances such as tungsten or gold beads.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various mutes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

Preferred promoters for gene therapy for use in this invention include cytomegalovirus (CMV) promoter/enhancer, long terminal repeat (LTR) of retroviruses, keratin 14 promoter, and a myosin heavy chain promoter. Tissue specific promoters may be advantageous for disease or conditions where localized VEGF-B expression is desirable.

Therapeutic Formulations

Therapeutic formulations of the compositions useful for practicing the present invention such as VEGF-B polypeptides, polynucleotides, or antibodies may be prepared for storage by mixing the selected composition having the desired degree of purity with optional physiologically pharmaceutically-acceptable carriers, excipients, or stabilizers (Remington's Pharmaceutical Sciences, 18th edition, A. R. Gennaro, ed., Mack Publishing Company (1990)) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The composition to be used for in vivo administration should be sterile. This is readily accomplished by filtration through sterile filtration membranes, prior to or following lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle. The route of administration of the composition is in accord with known methods, e.g. oral, injection or infusion by intravenous, intraperitoneal, intracerebral, intramuscular, intraocular, intraarterial, or intralesional routes, or by sustained release systems or implantation device. Where desired, the compositions may be administered continuously by infusion, bolus injection or by implantation device.

Suitable examples of sustained-release preparations include semi-permeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., Biopolymers, 22: 547-556 (1983)), poly(2-hydroxyethyl-methacrylate) (Langer, et al., J. Biomed. Mater. Res., 15:167-277 (1981) and Langer, Chem. Tech., 12:98-105 (1982)), ethylene vinyl acetate (Langer, et al., supra) or poly-D(–)-3-hydroxybutyric acid (EP 133,988). Sustained-release compositions also may include liposomes, which can be prepared by any of several methods known in the art (e.g., DE 3,218,121; Epstein, at al., Proc. Natl. Acad. Sci. USA, 82:3688-3692 (1985); Hwang, et al., Proc. Natl. Acad. Sci. USA, 77:4030-4034 (1980); EP 52,322; EP 36,676; EP 88,046; EP 143,949).

An effective amount of the compositions to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage may range from about 1 μg/kg to up to 100 mg/kg or more, depending on the factors mentioned above. Typically, a clinician will administer the composition until a dosage is reached that achieves the desired effect. The progress of this therapy is easily monitored by conventional assays designed to evaluate blood glucose levels or other particular conditions of interest in a particular subject.

Pharmaceutical compositions may be produced by admixing a pharmaceutically effective amount of VEGF-B protein with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

VEGF-B can be used directly to practice materials and methods of the invention, but in preferred embodiments, the compounds are formulated with pharmaceutically acceptable diluents, adjuvants, excipients, or carriers. The phrase "pharmaceutically or pharmacologically acceptable" refers to molecular entities and compositions that do not produce adverse, allergic, or other untoward reactions when administered to an animal or a human, e.g., orally, topically, transdermally, parenterally, by inhalation spray, vaginally, rectally, or by intracranial injection. (The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and/or surgical implantation at a particular site is contemplated as well.) Generally, this will also entail preparing compositions that are essentially free of pyrogens, as well as other impurities that could be harmful to humans or animals. The term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Routes of Administration

The therapeutic compositions are administered by any route that delivers an effective dosage to the desired site of action, with acceptable (preferably minimal) side-effects. Numerous routes of administration of agents are known, for example, oral, rectal, transmucosal, or intestinal administration; parenteral delivery, including intramuscular, subcutaneous, intramedullary injections, as well as intrathecal, intraperitoneal, intranasal, cutaneous or intradermal injections; inhalation, and topical application. However, localized routes of administration directed to the tissue(s) or organ(s) that are the target of treatment is preferred. This may be the brain, or spine in certain neurodegenerative disorders; the muscles and/or heart in other disorders; the liver or kidneys, the intestine, etc.

Therapeutic dosing is achieved by monitoring therapeutic benefit in terms of any of the parameters outlined herein (speed of wound healing, reduced edema, reduced complications, etc.) and monitoring to avoid side-effects. Preferred dosage provides a maximum localized therapeutic benefit with minimum local or systemic side-effects. Suitable human dosage ranges for the polynucleotides or polypeptides can be extrapolated from these dosages or from similar studies in appropriate animal models. Dosages can then be adjusted as necessary by the clinician to provide maximal therapeutic benefit for human subjects.

Compositions and Formulations

Compositions for use in accordance with the present invention may be formulated in a conventional manner using one or more physiologically acceptable carriers comprising excipients and auxiliaries that facilitate processing of a therapeutic composition into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When a therapeutically effective amount of a composition of the present invention is administered by e.g., intradermal, cutaneous or subcutaneous injection, the composition is preferably in the form of a pyrogen-free, parenterally acceptable aqueous solution. The preparation of such parenterally acceptable protein or polynucleotide solutions, having due regard to pH, isotonicity, stability, and the like, is within the skill in the art. A preferred composition should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art. The agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compositions can be formulated readily by combining the active compounds with pharmaceutically acceptable carriers well known in the art. Such carriers enable the compounds of the invention to be formulated as tablets, pills, dragees, powders, capsules, liquids, solutions, gels, syrups, slurries, suspensions and the like, for oral ingestion by a patient to be treated.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas.

Pharmaceutical formulations for parenteral administration include aqueous solutions of the compositions in water-soluble form. Optionally, the suspension may also contain suitable stabilizers or agents which increase the solubility of the compositions to allow for the preparation of highly concentrated solutions. Alternatively, the active ingredient may be in powder form for constitution with a suitable vehicle, e.g., sterile pyrogen-free water, before use The compositions may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions also may comprise suitable solid or gel phase carriers or excipients.

The compositions of the invention may be in the form of a complex of the protein(s) or other active ingredient of present invention along with protein or peptide antigens.

The compositions may include a matrix capable of delivering the protein-containing or other active ingredient-containing composition to the site of tissue damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties.

The composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects.

Techniques for formulation and administration of the therapeutic compositions of the instant application may be found in "Remington's Pharmaceutical Sciences," Mack Publishing Co., Easton, Pa., latest edition. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

EXAMPLES

Example 1

Materials and Methods

A. Expression of Fatty Acid Transport Proteins in Mice Hearts Deficient of VEGF-B Total cellular RNA was isolated from normal and VEGF-B-/- mice hearts (Aase et al., Circ., 104:358-364, 2001) using the RNeasy kit (Qiagen). The integrity of the total RNAs were analyzed on denaturing formaldehyde gels. Complementary DNA was prepared from 3 µg of DNase treated RNA and SuperScriptII Reverse Transcriptase (Invitrogen) according to the manufacturer's instructions. PCR was performed on reverse transcripts using primer pairs listed in Table 1. All sequences were checked for specificity using BLAST analysis.

Quantitative real-time PCR was performed in duplicates using 5 µl samples of cDNA and 12.5 µl of 2× Platinum SYBR Green Supermix (Invitrogen) in a total reaction of 25 µl that contained 200 nM of forward and reverse primer. Reactions were run and analyzed using Rotor-Gene RG-3000A (Corbett Research). Melting curves were run on all reactions to ensure amplification of a single product (data not shown). Samples were normalized to parallel reactions using primers specific for actin (Table 1). The fold increase/decrease of fatty-acid transport proteins in VEGF-B-/- relative to normal hearts was determined using the $2^{-\Delta\Delta Ct}$ method (Livak et al., Methods, 25:402-406, 2001). The average values and standard deviations were based on three independent experiments.

B. Protein Expression of Fatty Acid Handling Proteins in Mice Deficient of VEGF-B Hearts from VEGF-B+/+ and -/- mice were homogenized in lysis buffer containing 50 mM Tris-HCl pH 8.0, 150 mM NaCl, 1% Triton X-100, 0.5% deoxycholate, 0.1% SDS, 0.5 mmol/L and protease inhibitors (Complete; Roche). The heart lysates were incubated at 4° C. for 30 minutes and supernatants were collected in two centrifugation steps at 10 000×g for 20 minutes at 4° C. Aliquots were subjected to sodium dodecyl sulfate-polyacrylamide gel electrophoresis (SDS-PAGE) (15%) under reducing conditions. Immunoblotting was performed using a rabbit polyclonal antibody raised against amino acids 41-140 of FATP4 of human origin (Santa Cruz Biotechnology Inc., 1 µg Ig/ml) or a rabbit polyclonal antibody raised human endothelial lipase amino acids 19-32 (Cayman Chemical, 1.5 µg Ig/ml) followed by detection with HRP-coupled secondary antibody (Amersham Biosciences). Bound antibodies were visualized using ECL+ (Amersham Biosciences). As loading control, the ER protein calnexin was visualized using a rabbit antiserum against human calnexin.

C. Expression of FATP4 and LPL in Pig Hearts Overexpressing VEGF-B-186

Pig hearts transduced with an adenovirus encoded LacZ or hVEGF-B$_{186}$ were received from Seppo Herttuala. Total cellular RNA was isolated from the transduced pig hearts and quantitative real-time PCR was performed as described before. The primer pairs used are listed below in Table 1.

TABLE 1

| Name | Oligonucleotides | Sequence Identifier |
|---|---|---|
| mFATP1 | Sense: 5'-tcaatgtaccaggaattacagaagg-3' | 10 |
| | Antisense: 5'-tctccaggctcagagtcagaag-3' | 11 |
| mFATP2 | Sense: 5'-ttcctgaggatacaagataccattg-3' | 12 |
| | Antisense: 5'-ttctttctggaaatgtcatgagc-3' | 13 |
| mFATP3 | Sense: 5'-ctctgaacctggtgcagtcta-3' | 14 |
| | Antisense: 5'-tcgaaggtctccagacaggag-3' | 15 |
| mFATP4 | Sense: 5'-gcaagtcccatcagcaactg-3' | 16 |
| | Antisense: 5'-gggggaaatcacagcttctc-3' | 17 |
| mFATP5 | Sense: 5'-gctataccagcatgtccgctc-3' | 18 |
| | Antisense: 5'-gtggtcagagattccaggttcc-3' | 19 |

TABLE 1-continued

| Name | Oligonucleotides | Sequence Identifier |
|---|---|---|
| mFATP6 | Sense:<br>5'-tacaaccaagtggtgacatctctg-3'<br>Antisense:<br>5'-aatctcttcggtcaatgggac-3' | 20<br><br>21 |
| mLPL | Sense:<br>5'-gcgagaacattcccttcacc-3'<br>Antisense:<br>5'-aacactactgagtcctttccc-3' | 22<br><br>23 |
| mCD36 | Sense:<br>5'-gatgagcataggacatacttagatgtg-3'<br>Antisense:<br>5'-caccactccaatcccaagtaag-3' | 24<br><br>25 |
| mβ-actin | Sense:<br>5'-actcttccagccttccttc-3'<br>Antisense:<br>5'-atctccttctgcatcctgtc-3' | 26<br><br>27 |
| mVEGFR-1 | Sense:<br>5'-ttgaggagctttcaccgaac-3'<br>Antisense:<br>5'-ggaggagtacaacaccacgg-3' | 28<br><br>29 |
| mVEGFR-2 | Sense:<br>5'-agtaaaagcagggagtctgtgg-3'<br>Antisense:<br>3'-agcacctctctcgtgatttcc-3' | 30<br><br>31 |
| pFATP4 | Sense:<br>5'-tggtccgtgtcaacgagg-3'<br>Antisense:<br>5'-ggtggacacgttctcgcc-3' | 32<br><br>33 |
| pβ-actin | Sense:<br>5'-atggaatcctgcggcatc-3'<br>Antisense:<br>5'-gcttgctgstccacatctgc-3' | 34<br><br>35 |
| p-LPL | Sense:<br>5'-catcccttttcaccctgcc-3'<br>Antisense:<br>5'-tgtcgtggcatttcacaaac-3' | 36<br><br>37 |
| pPECAM | Sense:<br>5'-agcaccacttctgaactccaac-3'<br>Antisense:<br>5'-ctgctctgcggtcctaagtc-3' | 38<br><br>39 |

Protein samples from LacZ or hVEGF-$B_{186}$ transduced pig hearts were prepared as described before and analyzed on 15% SDS-PAGE followed by Western blot analysis using anti-FATP4 or LPL polyclonal antibodies.

D. Expression of Fatty Acid Transporting Proteins in Endothelial Cells

The pancreatic islet endothelial cells MILE SVEN 1 (MS1) (Arbiser et al., Am. J. Pathol., 156:1469-1476, 2000) were grown in Dulbecco's modified Eagle's medium (DMEM) containing 10% FCS, glutamine and antibiotics. The growth media was changed every second day and the cells were cultured until confluency. Total RNA was isolated from the MS1 cells using the RNeasy kit (Qiagen). The integrity of the total RNAs were analyzed on denaturing formaldehyde gels. Complementary DNA was prepared from 3 μg of DNase treated RNA and SuperScriptII Reverse Transcriptase (Invitrogen) according to the manufacturer's instructions. Q-PCR was performed on reverse transcripts using primer pairs listed in Table 1. All sequences were checked for specificity using BLAST analysis. For stimulation with VEGF-B, the cultures were washed with PBS, and the MS1 cells were then starved in DMEM containing 0.5% FCS for 24 hrs. After starvation, the medium was replaced with DMEM containing 0.5% FCS containing 50 ng/mL, or 100 ng/mL of human recombinant VEGF-$B_{167}$ and the cells were further incubated for an additional six or twenty-four hours. Total RNA was isolated and the integrity of the RNA was analyzed as described before. Complementary DNA was prepared from 3 μg of DNase treated RNA and SuperScriptII Reverse Transcriptase according to the manufacturer's instructions (Invitrogen). Quantitative real-time PCR was performed in duplicates using 5 μl samples of cDNA and 12.5 μl of 2× Platinum SYBR Green Supermix (Invitrogen) in a total reaction of 25 μl that contained 200 nM of forward and reverse primers. Reactions were run and analyzed using Rotor-Gene RG-3000A (Corbett Research). Melting curves were run on all reactions to ensure amplification of a single product (data not shown). Samples were normalized to parallel reactions using primers specific for actin (Table 1). The fold increase/decrease of FATP4 mRNAs in VEGF-B treated relative to non-treated cells was determined using the $2^{-\Delta\Delta Ct}$ method (Arbiser, supra).

E. Oil Red O Staining in VEGF-B+/+ and −/− Mice Hearts

Hearts from VEGF-$B^{+/+}$ and $^{-/-}$ mice were dissected carefully, free from any visible fat and blood, washed in PBS and embedded in Tissue-Tek (Sakura Finetek). Serial sections (8-12 μm) were mounted on Superfrost+ glass slides. Oil red O (Sigma Aldrich) was dissolved to a stock solution by adding 2.5 g Oil red. 0 to 400 ml 2-isopropanol. Prior to staining, a working solution containing 18 ml oil red O stock solution and 12 ml deionized water, was prepared. This solution was passed through a 0.45 μM filter (Sarstedt) to remove crystallized oil red O. The heart sections were incubated in Oil red O working solution for 5 min at RT and washed in 10 min with running tap water. In order to visualize nuclei the glass slides were counterstained in Mayer's Hematoxylin solution for 15 seconds followed by a quick rinse in saturated Lithium carbonate solution. Slides were carefully rinsed in tap water and the stained sections were embedded in water-soluble mounting medium and analyzed using bright-field microscopy.

F. Expression of Fatty-Acid Transport Proteins in Tumors Over-Expressing VEGF-B

The fibrosarcoma cell line T241 was transfected with a mammalian expression vector encoding either for VEGF-$B_{167}$, or VEGF-$B_{186}$, or empty vector (mock) using cationic lipid reagent. Various stable clones were selected, expanded and analyzed for expression of exogenous VEGF-B. Two clones of each expression vector were chosen for the subsequent experiments. $10^6$ cells of the various clones were injected subcutaneously at the back of syngenic mice. After 15 days the grown tumors were excised and immediately snap frozen (U.S. Patent Publication No. 2005-0214280, the disclosure of which is incorporated herein by reference). Total RNA was isolated from the tumors using TRIzol reagent (Invitrogen) according to the manufacturer's protocol. The integrity of the total RNA preparations was analyzed on denaturing formaldehyde gels. Complementary DNA was prepared from 3 μg of DNase treated RNA and SuperScriptII Reverse Transcriptase (Invitrogen) according to the manufacturer's instructions.

Quantitative real-time PCR was performed in duplicates using 5 μl samples of cDNA and 12.5 μl of 2× Platinum SYBR Green Supermix (Invitrogen) in a total reaction of 25 μl that contained 200 nM of forward and reverse primer. Reactions were run and analyzed using Rotor-Gene RG-3000A (Corbett Research). Melting curves were run on all reactions to ensure amplification of a single product. Samples were normalized to parallel reactions using primers specific for actin (see Table 1). The fold increase/decrease of fatty-acid handling proteins in the VEGF-B overexpressing tumors relative to mock were determined using the $2^{-\Delta\Delta Ct}$ method (Arbiser, supra). The average values and standard deviations were each based on a group of four different tumors.

Example 2

Expression of Components of the Fatty Acid Transporting Machinery in Normal and Transgenic Mice To investigate if genes that are involved in fatty acid uptake and transport are potential down stream targets for VEGF-B, their expression was analyzed in hearts from normal, VEGF-B deficient, and transgenic mice with heart-specific over-expression of VEGF-B.

Conventional PCR was used to establish the gene expression patterns of various FATP members, and CD36 in normal mouse heart. Transcripts for FATP1, 2, 3, 4 and 6, as well as, CD36, the FATP co-receptor (Greenwalt et al., J. Clin. Invest., 96:1382-1388, 1995, the disclosure of which is incorporated herein by reference), were detected in the murine heart. NO transcript for FATP5 was found in the murine heart. However, FATP5 has been reported to be exclusively expressed in the liver (Hirsch et al., Proc. Natl. Acad. Sci. USA, 95:8625-8629, 1998). Quantitative real-time RT-PCR (Q-PCR) was used to compare the absolute transcript abundance of FATPs, CD36, and LPL in normal and VEGF-B$^{-/-}$ mice hearts. In hearts lacking VEGF-B, FATP4 mRNA was reduced to approximately 50%. FATP1, 3 and 6 were also down-regulated, however, to a lesser extent (expression reduced to approximately 70-80%). In contrast, no significant change in expression levels of FATP2 and CD36 were detected. Analysis of LPL mRNA demonstrated that this transcript is also down-regulated in VEGF-B deficient hearts (expression reduced to approximately 60%).

To analyze whether over-expression of VEGF-B in mouse heart resulted in increased expression of the FATPs and in CD36, we analyzed the transcript abundance of FATP4 in VEGF-B heart-specific transgenic mice by Q-PCR. These animals express human VEGF-B under the c-myosine heavy chain promoter (reference to be added) which gives a heart-specific expression of the transgene. Analyses of hearts from females and males with one (heterozygous), or two copies of the transgene (homozygous), demonstrated that FATP4 expression is controlled in a 15 gene-dose specific manner in both sexes with 3× upregulation in the homozygous animals, and 1,5× upregulation in the heterozygous animals (FIG. 4).

To analyze if protein expression levels of FATPs, exemplified by FATP4, and LPL were regulated in accordance with the corresponding transcript levels as measured by the QPCR analyses, protein aliquots from normal and VEGF-B deficient hearts were subjected to immunoblotting analyses using antibodies specific to FATP4 and LPL, respectively. As a loading control the blots were reprobed with antibodies to calnexin.

The results demonstrate that both FATP4 protein, as well as LPL protein, were down-regulated in VEGF-B deficient animals.

Example 3

Expression of FATP4 and LPL in Pig Hearts Transduced with Adenovirus Encoding VEGF-B VEGF-B protein or VEGF-B generated from adenoviruses has a remarkable capacity to stimulate neovascularization in mouse heart (see U.S. Patent Publication NO. 2005-0214280), and in pig heart. The pig heart receives several injections of adenoviruses (in total 1×10$^{12}$ particles) using a catheter-based system. Seven days after the injection the pigs are killed and the hearts are removed for analyses. Analysis of transduced myocardium by Q-PCR revealed that FATP4 mRNA is upregulated approximately 30-fold in VEGF-B transduced hearts compared to hearts receiving an identical injection of adenoviruses expressing lacZ only. As endothelial cells become more abundant in the VEGF-B transduced hearts due to the neovascularization, control analyses by Q-PCR of PECAM expression, an endotheial cell marker, showed an approximate 3× upregulation. Thus, if all upregulation of FATP4 mRNA occurs in the endothelial cells of the heart, the specific upregulation in this cell compartment is consequently 9-10 fold.

Similar analyses of LPL expression by Q-PCR analysis showed that LPL mRNA is upregulated. Analysis of the FATP4 and LPL protein levels by immunoblotting demonstrated that both proteins were sharply upregulated in VEGF-B 186 transduced myocardium. In conclusion, these analyses confirm and extend the previous data showing that FATPs and LPL are both regulated by VEGF-B.

Example 4

Expression of Fatty Acid Transporters and LPL in Endothelial Cells

In order to be taken up by the energy-requiring parenchymal cells of the heart, skeletal muscle, brain, stomach, and intestines, plasma-derived fatty acids must first transverse the endothelial cell layer, and this transcellular transport is mediated by specific fatty acid transporters (Van der Vusse et al., Adv. Exp. Med. Biol., 441:181-191, 1998). The endothelial cell line MS1 was used to investigate the expression of FATPs, CD36, and LPL in the capillary endothelium. The presence of the VEGF receptors, VEGFR-1 and VEGFR-2, in MS1 cells was confirmed by conventional PCR of cDNA generated from MS1 cells. Both receptors were found to be expressed in MS1 cells. Of the various fatty acid transporters that were analyzed, FATP1, 3, and 4 were easily detected in MS1 cells, and may thus be a potential downstream target for VEGF-B. CD36 was not expressed in MS1 cells. It has been reported that the occurrence of CD36 in the endothelium is tissue specific with expression restricted to the capillaries of adipose tissue and cardiac and skeletal muscle (Greenwalt, supra).

Example 5

Stimulation of FATP and LPL Expression in Endothelial Cells with VEGF-B

To investigate if expression of FATP1, 3, and 4 in endothelial MS1 cells is directly regulated by VEGF-B. MS1 cells were incubated with human recombinant VEGF-B for 20 hours. By Q-PCR analysis the relative expression of FATP mRNAs in VEGF-B treated, and non-treated MS1 cells was compared. The expression of FATP4 mRNA was increased 3.3-fold in MS1 cells treated with VEGF-B, compared to the untreated control, suggesting, that VEGF-B can indeed stimulated the expression of FATP4 in endothelial cells. Similar analyses of FATP1 and 3 mRNAs revealed an induction of 5.0 and 2.5-fold, respectively. Thus, all FATPs expressed in the MS1 cells are induced by VEGF-B treatment.

Analysis of LPL expression by Q-PCR similarly showed an induction of 2.5 fold in the MS1 cells upon VEGF-B treatment. To analyze the specificity of VEGF-B mediated induction of FATP4 mRNA, several VEGFs including VEGF-B, P1GF, VEGF-A, and VEGF-E, were applied onto MS1 cells and induction of FATP4 mRNA was measured as above. The results demonstrate that VEGF-B exert a specific effect on induction of FATP4 mRNA as the other VEGFR-1 ligands, P1GF and VEGF-A, failed to induced FATP4 mRNA. VEGF-E, being a VEGFR-2 specific ligand, also failed to induced FATP4 mRNA. In summary these data demonstrate that VEGF-B exert a specific effect on the induction of the FATPs and that its function is distinct from the other VEGFR-1 ligands.

Example 6

Expression of Fatty Acid Transporters in Tumors Over-Expressing VEGF-B

In order to further establish a link between the FATPs and VEGF-B, the expression of fatty acid transporting proteins was investigated in tumors over-expressing two biological isoforms of VEGF-B; VEGF-$B_{167}$ and VEGF-$B_{186}$. Tumors overexpressing VEGF-$B_{186}$ grow significantly faster than tumors transfected with VEGF-$B_{167}$, or mock transfected (unpublished observation, and previous Ludwig filing/application LUD5893). By Q-PCR analysis the relative expression of various FATPs and CD36 were compared in the VEGF-B over-expressing tumors. The expression of FATP1 was increased 2-2.5 folds in tumors over-expressing VEGF-B156. No significant up-regulation was found for FATP2, 3, 4, or 6 or for CD36 in the VEGF-B overexpressing tumors. This suggests that VEGF-B can target various members of the FATP family and this may depend on the tissue.

Example 7

Evidence for a Direct Role of VEGF-B in Tissue Accumulation of Lipids

All evidence presented so far suggest an important role of VEGF-B in tissue uptake of fatty acids by controlling the expression of FATPs and LPL in endothelial cells. To directly demonstrate that is the case, tissue sections from normal and VEGF-B deficient animals were stained with Oil Red O, a dye that incorporated into lipid droplets and stains intensely red.

The number of Oil red O-stained lipid droplets in heart tissues from normal and VEGF-B deficient mice was quantified by manually counting the number of stained droplets in representative fields in the microscope. The results demonstrate that VEGF-B deficient animals have lost more than 60% of the number of lipid droplets in heart tissue compared with normal mice. It is also observed that the average diameter of the droplets in the VEGF-B deficient mice is much smaller. In summary, this shows that VEGF-B controls lipid accumulation in heart tissue by regulating the FATPs and other components in the machinery that controls uptake of lipids from the blood stream.

Example 8

Expression of FATPs in Liver from Normal and VEGF-B Deficient Mice

Since the liver is the major lipid metabolizing organ in the body it was of interest to compare the expression levels of the FATPs in normal and VEGF-B deficient mice. Analyses by QPCR showed that the relative expression of most of the FATPs were down-regulated in the VEGF-B deficient mice. The exception was FATP1 that was unchanged. The expression of CD36 was slightly upregulated in VEGF-B deficient mice.

As many of the FATPs were down-regulated in livers from VEGF-B deficient mice, the lipid accumulation in liver was examined by oil Red O staining of cryosections. The results show that lipid accumulation is drastically reduced in livers from VEGF-B deficient animals. Quantification of the red pixels in several representative microphotographs using the graphic software Photoshop (Adobe Inc.) demonstrated that livers from VEGF-B deficient mice have 70-80% less lipids.

Example 9

Expression of a Glucose Transporter, Glut4, in Heart of Normal and VEGF-B Deficient Heart It is well known in the literature that lipid deprivation in metabolically very active tissues, like the heart, will force these tissues to change their energy metabolism from being mainly based on lipids to a carbohydrate/glucose-based metabolism. Conversely, carbohydrate/glucose deprivation forces the tissue to change the energy metabolism to be based on lipids. Since loss of VEGF-B apparently leads to drastically diminished tissue accumulation of lipids it is contemplated that genes involved in carbohydrate/glucose metabolism should be up-regulated. To test this hypothesis, the expression of a major glucose transport in heart, glucose transporter 4 (Glut4), was analyzed. Analysis of Glut4 expression in normal and VEGF-B deficient hearts by QPCR revealed a significant upregulation of Glut4 transcripts in VEGF-B deficient animals. The primers used in the analysis was; forward 5' CTGTCGCTGGTTTCTCCAAC-'3 (SEQ ID NO: 40) and reverse 5' AAGGGAAGGTGTCCGTCG 3' (SEQ ID NO: 41). In conclusion, the results demonstrate that a predicted metabolic change occurred in the VEGF-B deficient animals in that they convert their metabolism to be more dependent on carbohydrate/glucose that their normal counterpart. The reason for this is the apparent inability of the VEGF-B deficient animals to accumulate sufficient amounts of lipids from the circulation to support efficient energy production Example 10

FATPs in Brain

VEGF-B is abundantly expressed in brain and it is of interest to investigate the expression of the FATPs in this tissue. Analyses by conventional PCR showed that all FATPs, except FATP6, are expressed in brain. Given that many of the FATPs are regulated by VEGF-B in other tissue it is reasonable to believe that at least some of them are regulated by VEGF-B in brain as well.

Sequence Listing

| Sequence Identifier | Description | Sequence |
|---|---|---|
| 1. | VEGF-B (human) DNA Genbank Acc. No.: NM_003377 | gcgatgcgggcgccccggcgggcggccccggcgggcaccatg agccctctgctccgccgcctgctgctcgccgcactcctgcagctggc ccccgcccaggccc ctgtctcccagcctgatgcccctggccaccag aggaaagtggtgtcatggatagatgtgtatactcgcgctacctgccag cccgggaggtggtggtgcccttgactgtggagctcatgggcaccg tggccaaacagctggtcccagctgcgtgactgtgcagcgctgtggt ggctgctgccctgacgatggcctggagtgtgtgcccactgggcagc accaagtccggatgcagatcctcatgatccggtacccgagcagtca gctggggagatgtccctggaagaacacagccagtgtgaatgcag acctaaaaaaaaggacagtgctgtgaagccagacagggctgccact ccccaccaccgtccccagcccgttctgttccgggctgggactctgc ccccggagcaccctccccagctgacatcacccatcccactccagcc ccaggcccctctgcccacgctgcacccagcaccaccagcgccctg accccggacctgccgctgccgctgccgacgccgcagcttcctccg ttgccaagggcggggcttagagctcaacccagacacctgcaggtgc cggaagctgcgaaggtgacacatggcttttcagactcagcagggtg acttgcctcagaggctatatcccagtggggaacaaagaggagcct ggtaaaaaacagccaagcccccaagacctcagcccaggcagaag ctgctctaggacctgggcctctcagagggctcttctgccatcccttgtc tccctgaggccatcatcaaacaggacagagttggaagaggagactg ggaggcagcaagaggggtcacataccagctcaggggagaatgga gtactgtctcagtttctaaccactctgtgcaagtaagcatcttacaactg gctcttcctcccctcactaagaagacccaaacctctgcataatgggatt tgggctttggtacaagaactgtgaccccccaaccctgataaaagagat ggaaggaaaaaaaaaaaaaaaaaaaaaaaaaaaaaaaaaaaaaa aaaaaaaaaaaaaaa |
| 2. | VEGF-B (human) AA Genbank Acc. No.: NM_003377 | MSPLLRRLLLAALLQLAPAQAPVSQPDAPG HQRKVVSWIDVYTRATCQPREVVVPLTVEL MGTVAKQLVPSCVTVQRCGGCCPDDGLEC VPTGQHQVRMQILMIRYPSSQLGEMSLEEH SQCECRPKKKDSAVKPDRAATPHHRPQPRS VPGWDSAPGAPSPADITHPTPGPSAHAAP STTSALTPGPAAAAADAAASSVAKGGA |
| 3. | VEGF-B$_{167}$ (human) AA Genbank Acc. No.: AAL79000 | MSPLLRRLLLAALLQLAPAQAPVSQPDAPG HQRKVVSWIDVYTRATCQPREVVVPLTVEL MGTVAKQLVPSCVTVQRCGGCCPDDGLEC VPTGQHQVRMQILMIRYPSSQLGEMSLEEH SQCECRPKKKDSAVKPDSPRPLCPRCTQHH QRPDPRTCRRRCRRRSFLRCQGRGLELNPDT CRCRKLRR |
| 4. | VEGF-B$_{186}$ (human) AA Genbank Acc. No.: AAL79001 | MSPLLRRLLLAALLQLAPAQAPVSQPDAPG HQRKVVSWIDVYTRATCQPREVVVPLTVEL MGTVAKQLVPSCVTVQRCGGCCPDDGLEC VPTGQHQVRMQILMIRYPSSQLGEMSLEEH SQCECRPKKKDSAVKPDRAATPHHRPQPRS VPGWDSAPGAPSPADITHPTPAPGPSAHAAP STTSALTPGPAAAAADAAASSVAKGGA |
| 5. | VEGF-B (mouse) DNA Genbank Acc No.: NM_011697 | ctcaggccgtcgctgcggcgctgcgttgcgctgcctgcgcccaggg ctcggagggggccgcggaggagccgccccctgcgccccgccc cgggtcccccgggccgcgccatggggctctggctgccgccgccc ccacgccgccgggctagggccatgcgggcgctcccggcgctcgc ccccgcgggcaccatgagccccctgctccgtcgcctgctgcttgtt gcactgctgcagctggctcgcacccaggcccctgtgtcccagtttga tggccccagccaccagaagaaagtggtgccatggatagacgtttatg cacgtgccacatgccagcccagggaggtggtggtgcctctgagcat ggaactcatgggcaatgtggtcaaacaactagtgcccagctgtgtga ctgtgcagcgctgtggtggctgctgccctgacgatggcctggaatgt gtgcccactgggcaacaccaagtccgaatgcagatcctcatgatcca gtacccgagcagtcagctgggggagatgtccctggaagaacacag ccaatgtgaatgcagaccaaaaaaaaaggagagtgctgtgaagcca gacaggggttgccataccccaccaccgtccccagcccgctctgttcc gggctgggactctacc ccgggagcatcctccccagctgacatcatccatcccactccagcccc aggatcctctgcccgccttgcacccagcgccgtcaacgccctgacc cccggacctgccgctgccgctgcagacgccgccgcttcctccattg ccaagggcggggcttagagctcaacccagacacctgtaggtgccg gaagccgcgaaagtgacaagctgctttccagactccacgggcccg gctgcttttatgccctgcttcacagggagaagagtggagcacaggc gaacctcctcagtctggggaggtcactgcccaggacctggaccttttta gagagctctctcgccatcttttatctcccagagctgccatctaacaattg tcaaggaacctcatgtctcacctcagggggccagggtactctctcactt |

Sequence Listing

| Sequence Identifier | Description | Sequence |
|---|---|---|
| | | aaccaccctggtcaagtgagcatcttctggctggctgtctcccctcact atgaaaaccccaaacttctaccaataacgggatttgggttctgttatga taactgtgacacacacacacactcacactctgataaaagagatggaa gacactaac |
| 6. | VEGF-B (mouse) AA Genbank Acc No.: NM_011697 | MSPLLRRLLLVALLQLARTQAPVSQFDGPS HQKKVVPWIDVYARATCQPREVVVPLSME LMGNVVKQLVPSCVTVQRCGGCCPDDGLE CVPTGQHQVRMQILMIQYPSSQLGEMSLEE HSQCECRPKKKESAVKPDRVAIPHHRPQPRS VPGWDSTPGASSPADIIHPTPAPGSSARLAPS AVNALTPGPAAAAADAAADDIAKGGA |
| 7. | VEGF-$B_{167}$ (mouse) AA | MSPLLRRLLLVALLQLARTQAPVSQFDGPS HQKKVVPWIDVYARATCQPREVVVPLSME LMGNVVKQLVPSCVTVQRCGGCCPDDGLE CVPTGQHQVRMQILMIQYPSSQLGEMSLEE HSQCECRPKKKESAVKPDSPRILCPPCTQRR QRPDPRTCRCRCRRRRFLHCQGRGLELNPD TCRCRKPRK |
| 8. | VEGF-$B_{186}$ (mouse) AA Genbank Acc. No.: U52820 | MSPLLRRLLLVALLQLARTQAPVSQFDGPS HQKKVVPWIDVYARATCQPREVVVPLSME LMGNVVKQLVPSCVTVQRCGGCCPDDGLE CVPTGQHQVRMQILMIQYPSSQLGEMSLEE HSQCECRPKKKESAVKPDRVAIPHHRPQPRS VPGWDSTPGASSPADIIHPTPAPGSSARLAPS AVNALTPGPAAAAADAAASSIAKGGA |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A method of reducing VEGF-B mediated lipid accumulation in heart or skeletal muscle tissue in a human subject comprising administering to the subject a composition comprising a VEGF-B neutralizing antibody that binds to human VEGF-B in an amount effective to reduce VEGF-B mediated lipid accumulation in heart or skeletal muscle tissue in the subject.

2. The method of claim 1 wherein the antibody is a monoclonal antibody.

3. The method of claim 1 wherein the antibody is a humanized antibody.

4. The method of claim 1 wherein the antibody binds to one or more of VEGF-B$_{167}$ and VEGF-B$_{186}$.

5. The method of claim 1 wherein the subject has type II diabetes.

6. The method of claim 5 wherein the antibody is administered in combination with an anti-diabetic agent.

7. The method of claim 6 wherein the antibody and the anti-diabetic agent are administered separately or in the form of a combination product.

8. The method of claim 6 wherein the anti-diabetic agent is selected from the group consisting of an insulin secretagogue, metformin, a peroxisome proliferators-activated receptor-γ agonist, an α-glucosidase inhibitor, and insulin.

9. A method of reducing plasma glucose in a human subject having an elevated plasma glucose level comprising administering to the subject a composition comprising a VEGF-B neutralizing antibody that binds to human VEGF-B in an amount effective to reduce the plasma glucose level of the subject.

10. The method of claim 9 wherein the elevated plasma glucose level is 200 mg/dL or more when measured by a random plasma glucose test or oral glucose tolerance test, or 126 mg/dL or more when measured by a fasting plasma glucose test.

11. The method of claim 9 wherein the antibody is a monoclonal antibody.

12. The method of claim 9 wherein the antibody is a humanized antibody.

13. The method of claim 9 wherein the antibody binds to one or more of VEGF-B$_{167}$ or VEGF-B$_{186}$.

14. The method of claim 9 wherein the subject has diabetes.

15. The method of claim 9 wherein the subject is at risk of diabetes.

16. The method of claim 9 wherein the antibody is administered in combination with a medicament that lowers blood glucose.

17. The method of claim 16 wherein the antibody and medicament are administered separately or in the form of a combination product.

18. The method of claim 14 wherein the antibody is administered in combination with an anti-diabetic agent.

19. The method of claim 18 wherein the antibody and the anti-diabetic agent are administered separately or in the form of a combination product.

20. The method of claim 18 wherein the anti-diabetic agent is selected from the group consisting of an insulin secretagogue metformin, a peroxisome proliferators-activated receptor-γ agonist, an α-glucosidase inhibitor, and insulin.

21. A method of treating type II diabetes comprising administering to a human subject having type II diabetes a composition comprising a VEGF-B neutralizing antibody that binds to human VEGF-B in an amount effective to ameliorate one or more symptoms of type II diabetes.

22. The method of claim 21 wherein the antibody is a monoclonal antibody.

23. The method of claim 21 wherein the antibody is a humanized antibody.

24. The method of claim 21 wherein the antibody binds to one or more of VEGF-B$_{167}$ and VEGF-B$_{186}$.

25. The method of claim 21 wherein the antibody is administered in combination with an anti-diabetic agent.

26. The method of claim 25 wherein the antibody and the anti-diabetic agent are administered separately or in the form of a combination product.

27. The method of claim 25 wherein the anti-diabetic agent is selected from the group consisting of an insulin secretagogue, metformin, a peroxisome proliferators-activated receptor-γ agonist, an α-glucosidase inhibitor, and insulin.

28. The method of claim 1 wherein the antibody is a human antibody.

29. The method of claim 9 wherein the antibody is a human antibody.

30. The method of claim 21 wherein the antibody is a human antibody.

* * * * *

UNITED STATES PATENT AND TRADEMARK OFFICE
CERTIFICATE OF CORRECTION

PATENT NO. : 8,383,112 B2
APPLICATION NO. : 13/343493
DATED : February 26, 2013
INVENTOR(S) : Ulf Eriksson Page 1 of 1

It is certified that error appears in the above-identified patent and that said Letters Patent is hereby corrected as shown below:

Title Page, item (63) delete "May 7, 2007," and insert --May 17, 2007,--.

Signed and Sealed this
First Day of December, 2015

Michelle K. Lee
*Director of the United States Patent and Trademark Office*

SEQUENCE LISTING

```
<160> NUMBER OF SEQ ID NOS: 42

<210> SEQ ID NO 1
<211> LENGTH: 1172
<212> TYPE: DNA
<213> ORGANISM: Homo sapiens

<400> SEQUENCE: 1
gcgatgcggg cgcccccggc gggcggcccc ggcgggcacc atgagccctc tgctccgccg      60
cctgctgctc gccgcactcc tgcagctggc ccccgcccag gcccctgtct cccagcctga     120
tgcccctggc caccagagga aagtggtgtc atggatagat gtgtatactc gcgctacctg     180
ccagccccgg gaggtggtgg tgcccttgac tgtggagctc atgggcaccg tggccaaaca     240
gctggtgccc agctgcgtga ctgtgcagcg ctgtggtggc tgctgccctg acgatggcct     300
ggagtgtgtg cccactgggc agcaccaagt ccggatgcag atcctcatga tccggtaccc     360
gagcagtcag ctggggagga tgtccctgga agaacacagc cagtgtgaat gcagacctaa     420
aaaaaaggac agtgctgtga gccagacag gctgccact ccccaccacc gtccccagcc     480
ccgttctgtt ccgggctggg actctgcccc cggagcaccc tccccagctg acatcaccca     540
tcccactcca gccccaggcc cctctgccca cgctgcaccc agcaccacca gcgccctgac     600
ccccggacct gccgctgccg ctgccgacgc cgcagcttcc tccgttgcca agggcggggc     660
ttagagctca acccagacac ctgcaggtgc cggaagctgc gaaggtgaca catggctttt     720
```

-continued

```
cagactcagc agggtgactt gcctcagagg ctatatccca gtgggggaac aaagaggagc    780
ctggtaaaaa acagccaagc ccccaagacc tcagcccagg cagaagctgc tctaggacct    840
gggcctctca gagggctctt ctgccatccc ttgtctccct gaggccatca tcaaacagga    900
cagagttgga agaggagact gggaggcagc aagagggtc acataccagc tcaggggaga     960
atggagtact gtctcagttt ctaaccactc tgtgcaagta agcatcttac aactggctct    1020
tcctcccctc actaagaaga cccaaacctc tgcataatgg gatttgggct ttggtacaag    1080
aactgtgacc cccaaccctg ataaaagaga tggaaggaaa aaaaaaaaaa aaaaaaaaa     1140 aaaaaaaaaa aaaaaaaaaa aaaaaaaaaa aa                                  1172
```

<210> SEQ ID NO 2
<211> LENGTH: 207
<212> TYPE: PRT
<213> ORGANISM: Homo sapiens

<400> SEQUENCE: 2

```
Met Ser Pro Leu Leu Arg Arg Leu Leu Leu Ala Ala Leu Leu Gln Leu
  1               5                  10                  15

Ala Pro Ala Gln Ala Pro Val Ser Gln Pro Asp Ala Pro Gly His Gln
                 20                  25                  30

Arg Lys Val Val Ser Trp Ile Asp Val Tyr Thr Arg Ala Thr Cys Gln
             35                  40                  45

Pro Arg Glu Val Val Val Pro Leu Thr Val Glu Leu Met Gly Thr Val
         50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
        130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
                180                 185                 190

Ala Ala Ala Asp Ala Ala Ala Ser Ser Val Ala Lys Gly Gly Ala
            195                 200                 205
```

<210> SEQ ID NO 3
<211> LENGTH: 188
<212> TYPE: PRT
<213> ORGANISM: Homo sapiens

<400> SEQUENCE: 3

```
Met Ser Pro Leu Leu Arg Arg Leu Leu Leu Ala Ala Leu Leu Gln Leu
  1               5                  10                  15

Ala Pro Ala Gln Ala Pro Val Ser Gln Pro Asp Ala Pro Gly His Gln
                 20                  25                  30

Arg Lys Val Val Ser Trp Ile Asp Val Tyr Thr Arg Ala Thr Cys Gln
             35                  40                  45
```

```
Pro Arg Glu Val Val Pro Leu Thr Val Glu Leu Met Gly Thr Val
 50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 4
<211> LENGTH: 207
<212> TYPE: PRT
<213> ORGANISM: Homo sapiens

<400> SEQUENCE: 4

Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
             20                  25                  30

Arg Lys Val Val Ser Trp Ile Asp Val Tyr Thr Arg Ala Thr Cys Gln
         35                  40                  45

Pro Arg Glu Val Val Val Pro Leu Thr Val Glu Leu Met Gly Thr Val
     50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 5
<211> LENGTH: 1236
<212> TYPE: DNA
<213> ORGANISM: Mus musculus
```

```
<400> SEQUENCE: 5
ctcaggccgt cgctgcggcg ctgcgttgcg ctgcctgcgc ccagggctcg ggaggggggcc      60 gcggaggagc cgcccctgc gccccgcccc gggtccccgg gccgcgcca tggggctctg        120 gctgccgccg cccccacgc cgccgggcta gggccatgcg ggcgctcccg cgctcgccc        180 cccgcgggca ccatgagccc cctgctccgt cgcctgctgc ttgttgcact gctgcagctg      240
gctcgcaccc aggcccctgt gtcccagttt gatggcccca ccaccagaa gaaagtggtg       300 ccatggatag cgtttatgc acgtgccaca tgccagccca gggaggtggt ggtgcctctg       360
agcatggaac tcatgggcaa tgtggtcaaa caactagtgc ccagctgtgt gactgtgcag      420
cgctgtggtg gctgctgccc tgacgatggc ctggaatgtg tgcccactgg gcaacaccaa      480
gtccgaatgc agatcctcat gatccagtac ccgagcagtc agctggggga gatgtccctg      540
gaagaacaca gccaatgtga atgcagacca aaaaaaaagg agagtgctgt gaagccagac      600
agggttgcca taccccacca ccgtccccag ccccgctctg ttccgggctg ggactctacc      660
ccgggagcat cctccccagc tgacatcatc catcccactc cagccccagg atcctctgcc      720
cgccttgcac ccagcgccgt caacgccctg accccggac ctgccgctgc cgctgcagac       780
gccgccgctt cctccattgc caagggcggg gcttagagct caacccagac acctgtaggt     840
gccgaaagcc gcgaaagtga caagctgctt tccagactcc acgggcccgg ctgcttttat      900
ggccctgctt cacagggaga agagtggagc acaggcgaac ctcctcagtc tgggaggtca      960
ctgccccagg acctggacct tttagagagc tctctcgcca tcttttatct cccagagctg     1020
ccatctaaca attgtcaagg aacctcatgt ctcacctcag gggccagggt actctctcac     1080
ttaaccaccc tggtcaagtg agcatcttct ggctggctgt ctcccctcac tatgaaaacc     1140
ccaaacttct accaataacg ggatttgggt tctgttatga taactgtgac acacacacac     1200
actcacactc tgataaaaga gatggaagac actaac                                1236

<210> SEQ ID NO 6
<211> LENGTH: 207
<212> TYPE: PRT
<213> ORGANISM: Mus musculus

<400> SEQUENCE: 6

Met Ser Pro Leu Leu Arg Arg Leu Leu Leu Val Ala Leu Leu Gln Leu
  1               5                  10                  15

Ala Arg Thr Gln Ala Pro Val Ser Gln Phe Asp Gly Pro Ser His Gln
                 20                  25                  30

Lys Lys Val Val Pro Trp Ile Asp Val Tyr Ala Arg Ala Thr Cys Gln
             35                  40                  45

Pro Arg Glu Val Val Pro Leu Ser Met Glu Leu Met Gly Asn Val
         50                  55                  60

Val Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Glu Ser Ala Val Lys Pro Asp Arg Val Ala Ile Pro His His Arg
    130                 135                 140
```

```
Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
            180                 185                 190

Ala Ala Ala Asp Ala Ala Ala Ser Ser Ile Ala Lys Gly Gly Ala
        195                 200                 205

<210> SEQ ID NO 7
<211> LENGTH: 188
<212> TYPE: PRT
<213> ORGANISM: Mus musculus

<400> SEQUENCE: 7

Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
        35                  40                  45

Pro Arg Glu Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Glu Ser Ala Val Lys Pro Asp Ser Pro Arg Ile Leu Cys Pro Pro
    130                 135                 140

Cys Thr Gln Arg Arg Gln Arg Pro Asp Pro Arg Thr Cys Arg Cys Arg
145                 150                 155                 160

Cys Arg Arg Arg Arg Phe Leu His Cys Gln Gly Arg Gly Leu Glu Leu
                165                 170                 175

Asn Pro Asp Thr Cys Arg Cys Arg Lys Pro Arg Lys
            180                 185

<210> SEQ ID NO 8
<211> LENGTH: 207
<212> TYPE: PRT
<213> ORGANISM: Mus musculus

<400> SEQUENCE: 8

Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
        35                  40                  45

Pro Arg Glu Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
```

```
                85                  90                  95
Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Glu Ser Ala Val Lys Pro Asp Arg Val Ala Ile Pro His His Arg
    130                 135                 140

Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
            180                 185                 190

Ala Ala Ala Asp Ala Ala Ala Ser Ser Ile Ala Lys Gly Gly Ala
        195                 200                 205

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable amino acid
<220> FEATURE:
<221> NAME/KEY: MOD_RES
<222> LOCATION: (5)..(7)
<223> OTHER INFORMATION: variable amino acid
<220> FEATURE:
<221> NAME/KEY: MOD_RES
<222> LOCATION: (10)
<223> OTHER INFORMATION: variable amino acid

<400> SEQUENCE: 9

Pro Xaa Cys Val Xaa Xaa Xaa Arg Cys Xaa Gly Cys Cys
  1               5                  10

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcaatgtacc aggaattaca gaagg                                     25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tctccaggct cagagtcaga ag                                        22

<210> SEQ ID NO 12
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
ttcctgagga tacaagatac cattg                                           25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttctttctgg aaatgtcatg agc                                             23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctctgaacct ggtgcagctc ta                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcgaaggtct ccagacagga g                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcaagtccca tcagcaactg                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggggaaatc acagcttctc                                                 20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 18
gctataccag catgtccgct c                                            21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtggtcagag attccaggtt cc                                           22

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tacaaccaag tggtgacatc tctg                                         24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatctcttcg gtcaatggga c                                            21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcgagaacat tcccttcacc                                              20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aacactgctg agtcctttcc c                                            21

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 24
gatgagcata ggacatactt agatgtg                                          27

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caccactcca atcccaagta ag                                               22

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
actcttccag ccttccttc                                                   19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atctccttct gcatcctgtc                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttgaggagct ttcaccgaac                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggaggagtac aacaccacgg                                                  20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
```

```
agtaaaagca gggagtctgt gg                                              22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agcacctctc tcgtgatttc c                                               21

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tggtccgtgt caacgagg                                                   18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggtggacacg ttctcgcc                                                   18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atggaatcct gcggcatc                                                   18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcttgctgst ccacatctgc                                                 20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
catccctttc accctgcc                                                   18
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgtcgtggca tttcacaaac                                                   20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agcaccactt ctgaactcca ac                                                22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctgctctgcg gtcctaagtc                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtcgctgg tttctccaac                                                   20

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aagggaaggt gtccgtcg                                                     18

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 42

His His His His His His
 1               5